United States Patent
Krause et al.

(10) Patent No.: US 8,278,064 B2
(45) Date of Patent: Oct. 2, 2012

(54) METHOD FOR DETECTING A PROTEASE

(75) Inventors: Steffi Krause, London (GB); Dzaraini Kamarun, London (GB); Michael Watkinson, London (GB); Jacqueline Stair, London (GB)

(73) Assignee: Queen Mary & Westfield College, London (GB)

( * ) Notice: Subject to any disclaimer, the term of this patent is extended or adjusted under 35 U.S.C. 154(b) by 329 days.

(21) Appl. No.: 12/445,634

(22) PCT Filed: Oct. 16, 2007

(86) PCT No.: PCT/GB2007/003929
§ 371 (c)(1),
(2), (4) Date: Jul. 15, 2009

(87) PCT Pub. No.: WO2008/047095
PCT Pub. Date: Apr. 24, 2008

(65) Prior Publication Data
US 2010/0297683 A1    Nov. 25, 2010

(30) Foreign Application Priority Data
Oct. 16, 2006    (GB) .................................. 0620504.1

(51) Int. Cl.
*C12Q 1/37* (2006.01)
(52) U.S. Cl. ........................................................ 435/23
(58) Field of Classification Search ...................... 435/23
See application file for complete search history.

(56) References Cited

U.S. PATENT DOCUMENTS

| 6,974,707 B1 | 12/2005 | Barie et al. |
| 2009/0143658 A1 | 6/2009 | Petisce et al. |

FOREIGN PATENT DOCUMENTS

| EP | 0410323 A2 | 1/1991 |
| FR | 2872290 A1 | 12/2005 |
| GB | 2350677 A1 | 6/2000 |
| GB | 2350677 | * 12/2000 |
| WO | 87/07295 A1 | 12/1987 |
| WO | 89/03871 A1 | 5/1989 |
| WO | 99/63408 A1 | 12/1999 |
| WO | 00/75360 A2 | 12/2000 |

OTHER PUBLICATIONS

Coche-Guerente L. et al. Sol Gel Derived Composite Materials for the Construction of Oxidase/Peroxidase Mediatorless Biosensors. Chem Materials 1997 9:1348-1352.*
Saum, A. G. E., et al., Use of substrate coated electrodes and AC impedance spectroscopy for the detection of enzyme activity, Biosensors & Bioelectronics, 1998;13:511-18.
Kircher, M. F., et al., A dual fluorochrome probe for imaging proteases, Bioconjugate Chemistry, Mar. 2004;15 (2):242-248.
Aston, W. J., et al., Biosensors and Biofuel Cells, Biotech. Genet. Eng. Rev., 1984;1:89-120.
Davis, G., Electrochemical Techniques for the Development of Amperometric Biosensors, Biosensors, 1985;1:161-178.
Tarasevich, M. R., Bioelectrocatalysis, Bioelectrochemistry, 1985;10:231-295.
Ianniello, R. M., et al, Differential Pulse Voltammetric Study of Direct Electron Transfer in Glucose Oxidase Chemically Modified Graphite Electrodes, Anal. Chem., 1982;54:1098-1101.
Ianniello, R. M., et al., Immobilized Enzyme Chemically Modified Electrode as an Amperometric Sensor, Anal. Chem., 1981;53:2090-2095.
McNeil, C. J., et al., Electrochemical Sensors Based on Impedance Measurement of Enzyme-Catalyzed Polymer Dissolution: Theory and Applications, Anal. Chem., 1995;67:3928-3935.
Ho, W. O., et al., Electrochemical Sensor for Measurement of Urea and Creatinine in Serum Based on ac Impedance Measurement of Enzyme-Catalyzed Polymer Transformation, Anal. Chem., 1999;71:1940-1946.
Strohalm, J., et al., Poly[N-(2-hydroxypropyl)methacrylamide], Angewandte Makromolekulare Chemie, 1978;70:109-118.
Rejmanova, P., et al., Polymers Containing Enzymatically Degradable Bonds, 2a) Poly[N-(2-hydroxypropyl) methacrylamide] Chains Connected by Oligopeptide Sequences Cleavable by Chymotrypsin b), Makromal. Chem., 1981;182:1899-1915.
Ulbrich, K., et al., Polymers containing enzymatically degradable bonds. VI.Hydrophilic gels cleavable by chymotrypsin, Biomaterials, 1985;3;150-154.
Ulbridgh, K., et al., Polymers Containing Enzymatically Degradable Bonds, 3a) Poly[N-(2-hydroxypropyl) methacrylamide] Chains Connected by Oligopeptide Sequences Cleavable by Trypsin, Makromol. Chem., 1981;182:1917-1928.
Ulbridgh, K., et al., Polymers containing enzymatically degradable bonds V. Hydrophilic polymers degradable by papain, Biomaterials, 1980;1:199-204.
Duncan, R., et al., Degradation of Side Chains of N-(2-Hydroxypropyl Methacrylamide Copolymers by Lysosomal Enzymes, Biochemical and Biophysical Research Communications, May 4, 1980;94(1):284-290.
West, J. L., et al., Polymeric Biomaterials with Degradation Sites for Proteases Involved in Cell Migration, Macromolecules, 1999;32(1):241-244.
Mann, B. K., et al., Smooth muscle cell growth in photopolymerized hydrogels with cell adhesive and proteolytically degradable domains: synthetic ECM analogs for tissue engineering, Biomaterials, 2001;22:3045-3051.
Lutolf, M. P., et al., Synthesis and Physicochemical Characterization of End-Linked Poly(ethylene glycol)-copeptide Hydrogels Formed by Michael-Type Addition, Biomacromolecules, 2003;4:713-722.
Seliktar, D., et al., MMP-2 sensitive, VEGF-bearing bioactive hydrogels for promotion of vascular healing, J. Biomed. Mater. Res. A., 2004;68:706-716.
Arabuli, N., et al., Heterochain polymers based on natural amino acids. Synthesis and enzymatic hydrolysis of regular poly(ester amide)s based on bis(L-phyenylalanine) α, ω-alkylen diesters and adipic acid, Micromol. Chem. Phys., 1994;195:2279-2289.

(Continued)

*Primary Examiner* — Ralph Gitomer
(74) *Attorney, Agent, or Firm* — Pepper Hamilton LLP

(57) ABSTRACT

Methods for detecting proteases by contacting a sample to be assayed with a substrate at least partially coated with a film of a synthetic polymeric matrix, and measuring a signal output of the substrate is provided herein.

12 Claims, 12 Drawing Sheets

OTHER PUBLICATIONS

Brondsted, H., et al., Dextran hydrogels for colon-specific drug delivery III. In vitro and in vivo degradation, S.T.P. Pharma. Sciences, 1995;5(1):60-64.

Rickert, J., et al., Quartz crystal microbalances for quantitative biosensing and characterizing protein multilayers, Biosensors & Bioelectronics, 1997;12(7):567-575.

Toyama, S., et al., Surface design of SPR-based immunosensor for the effective binding of antigen or antibody in the evanescent field using mixed polymer matrix, Sensors and Actuators B, 1998;52:65-71.

Arwin, H., Spectroscopic ellipsometry and biology: recent developments and challenges, This Solid Films, 1998;313-314:764-774.

Auge, J., et al., Quartz crystal microbalance sensor in liquids, Sensors and Actuators B, 1994;18-19:518-522.

Sumner, C., et al., A Transduce Based on Enzyme-Induced Degradation of Thin Polymer Films Monitored by Surface Plasmon Resonance, Analytical Chemistry, Nov. 1, 2000;72(21):5225-5232.

Sabot, A., et al., Simultaneous Quartz Crystal Microbalance Impedance and Electrochemical Impedance Measurements. Investigation into the Degradation of Thin Polymer Films, Analytical Chemistry, Jul. 15, 2002;74 (14):3304-3311.

Krause, S., et al., Sensors Base don Thin Film Degradation, Encyclopedia of Sensors, American Scientific Publishers, 2005, ISBN:1-58883-056-X.

Korkmaz, B., et al., Discriminating between the Activities of Human Neutrophil Elastase and Proteinase 3 Using Serpin-derived Fluorogenic Substrates, Journal of Biological Chemistry, Oct. 18, 2002;277(42):39074-39081.

Castillo, M. J., et al., Sensitive Substrates for Human Leukocyte and Porcine Pancreatic Elastase: A Study of the Merits of Various Chromophoric and Fluorogenic Leaving Groups in Assays for Serine Proteases, Analytical Biochemistry, 1979;99:53-64.

McRae, B., et al., Studies on Reactivity of Human Leukocyte Elastase, Cathepsin G., and Porcine Pancreatic Elastase toward Peptides Including Sequences Related to the Reactive Site of alpha1-Protease Inhibitor (alpha1-Antitrypsin), Biochemistry, 1980;19:3973-3978.

Hunter, C. A., et al., Chemical Triple-Mutant Boxes for Quantifying Cooperativity in Intermolecular Interactions, Chem. Eur. J., 2002;8(23):5435-5446.

Ruys, L., et al., Polymer Drug Combinations. VII. Polymethacrylates and Modified Polysaccharides with Potential Antiarrhythmic Activity, Acta Pharmaceutica Technologica, 1983;29(2):105-112.

Park, Y., et al., Bovine primary chondrocyte culture in synthetic matrix metalloproteinase-sensitive poly (ethyleneglycol-)based hydrogels as a scaffold for cartilage repair, Tissue Engineering, Mar. 2004;10(3-4):515-522.

International Search Report, dated Jan. 23, 2008 for PCT/GB2007/003929.

* cited by examiner

METHOD FOR DETECTING A PROTEASE

CROSS-REFERENCE TO RELATED APPLICATIONS

This application is the U.S. National Stage filing of International Application Serial No. PCT/GB2007/003929 filed Oct. 16, 2007, which claims priority to GB Application No. 0620504.1 filed Oct. 16, 2006, each of which is incorporated herein by reference in its entirety.

The present invention relates to a method for the sensitive detection of a protease and apparatus for use in such a method.

Enzyme electrodes have been described previously, for example, in WO 87/07295 and WO 89/03871 which refer to enzyme electrodes capable of responding amperometrically to the catalytic activity of the enzyme in the presence of its respective substrates, wherein the enzyme is immobilised or adsorbed onto the surface of an electrically conductive support member. WO 00/75360 and GB-A-2350677 also describe the detection of enzymes using a protein cross-linked hydrogel.

The advantages of amperometric biosensors which incorporate enzymes have been reviewed (Aston & Turner, *Biotech. Genet. Eng. Rev.*, 1, 89-120, ed. G. Russell, Intercept, Newcastle-upon-Tyne (1984)); Davis G., *Biosensors*, 1, 161-178 (1985)). The biosensors vary in the mode of signal transduction and are loosely classified as (a) those in which the electrical response arises from the oxidation of a product of the enzyme reaction at an electrode, (b) "mediator assisted" reactions in which the electrons are transported from the enzyme to the electrode with the aid of an oxidation-reduction ("redox") reagent, or (c) "direct electron transfer" (DET) in which no such mediator assistance is required.

There are several disadvantages associated with the use of a mediator in signal transduction, including the possibility of the mediator leaching out from the region containing the biocatalyst, diffusion limitations of oxidised and/or reduced forms, and the inherent instability of the mediator itself. As a consequence, mediator-less biosensors have been targeted as an alternative (Tarasevich, *Bioelectrochemistry*, 10, 231-295 (1985)). Laneillo et al *Anal Chem*, 54, 1098-1101 (1982), describes mediator-less sensors in which glucose oxidase and L-amino acid oxidase were covalently bonded to a graphite electrode by the cyanuric chloride method. However, it was shown that these enzyme electrodes had only a limited working lifetime (Laniello & Yacynynch, *Anal Chem*, 53, 2090-2095 (1981)).

Up to now, mediator-less enzyme electrodes have often incorporated conducting organic polymers, e.g. structural units similar to that of methyl viologen, and/or conducting organic salts such as NMP TCNQ (N-methyl phenaziniumtetracyano-4-quinodimethane) which modify the properties of the electrode and fulfil the role of mediators. However, due to the instability of many conducting polymers, mediator-less electrodes of this type commonly exhibited a short half-life and were often oxygen sensitive.

More recently, a sensor principle based on measurement of capacitance changes produced during enzyme catalysed dissolution of polymer coatings on electrodes has been developed (McNeil et al *Anal Chem*, 67, 3928-3935 (1995)). Electrodes were coated with a biodegradable coating, a copolymer of methyl methacrylate and methacrylic acid. Dissolution is exemplified by a localised increase in pH near the surface of the coating due to the enzymatic reaction between urea and urease. Film degradation is accompanied by an increase in capacitance of up to four orders of magnitude. The method has been developed into a fast and simple disposable sensor for urea in serum and whole blood (Ho et al *Anal Chem* 71, 1940-1946 (1999)). Furthermore, it has been demonstrated that the high sensitivity and the fast response of this technique could be utilised for immunosensing using urease as the enzyme label.

However, there are several drawbacks associated with the above method, including the time required to produce the localised pH change to dissolve the polymer, the addition of an enzyme substrate and the need to wash (remove) excess enzyme label. Furthermore, following the polymer degradation by capacitance measurements only works effectively if the polymer coating is sufficiently insulating.

Synthetic polymer hydrogels have been extensively studied for various applications. Modifications with the inclusion of biomaterials such as peptides or polysaccharides convert the hydrogel into bioactive materials suitable for modulation of cellular functions such as cell adhesion, migration and proliferation. Incorporation of enzymatically degradable linkages in the side chains or cross-links renders the hydrogel susceptible to degradation by proteolytic processes; making it useful for applications in tissue remodelling and regeneration, duplication of wound healing and drug delivery.

Development of polymer hydrogels containing enzymatically degradable bonds has been carried out for many years, examples include studies on poly [N-(2-hydroxypropyl)-methacrylamide] (Strohalm, J.& Kopecek, J. *Angew. Makromol. Chem.*, 70, 109-118 (1978)). Enzymatically degradable hydrogels based on this polymer have been prepared by incorporating oligopeptide sequences containing 2-4 amino acid residues in the crosslink. Such polymers were intended to be used in drug delivery systems whereby retrieval of the exhausted depot would be eliminated. Substrates sensitive to proteases chymotrypsin (Rejmanova et al *Makromol. Chem.*, 182, 899-1915 (1981); Ulbrich et al *Biomaterials*, 3, 150-154 (1982)), trypsin (Ulbrich et al *Makromol. Chem.*, 182, 917-1928 (1981)), and papain (Ulbrich et al *Biomaterials*, 1, 199-204 (1980)) as well as lysosomal enzymes (Duncan et al *Biochem. Biophys. Res. Commun*, 94, 284-290 (1980)) have been studied. Hydrolysis of the substrates by their corresponding enzymes was characterized by measuring the time taken for complete dissolution of the gels; and from determination of the molecular weight distribution of the polymers using Gel Permeation Chromatography.

Copolymerized oligopeptides with poly (ethylene glycol), PEG, have also been made into various architectures. Telechelic BAB block copolymers of PEG and small peptides having sequences cleavable by collagenase and plasmin were synthesized (West, J. L. & Hubbell, J. A. *Macromolecules*, 32, 241-244 (1998)). The hydrogel materials produced upon crosslinking were targeted for use in wound healing and tissue engineering. Biospecific cell adhesion properties of hydrogels were achieved by grafting cell adhesive peptides such as RGD into hydrogels containing peptide units that are degraded by collagenase and elastase (Mann et al *Biomaterials*, 22, 3045-3051 (2001)). Collagenase and elastase are enzymes involved in cell migration.

Further hydrogels were also developed that can assist tissue regeneration by mimicking matrix metalloproteinase (MMP) mediated invasion of extracellular matrix (ECM). Linear oligopeptide substrates for MMPs were crosslinked with multiarm end functionalized PEG macromers (Lutolf, M. P.& Hubbell, J. A. *Biomacromolecules*, 4, 713-722 (2003)). Integrin-binding domains were attached in a pendant fashion to the hydrogel providing molecular signals for cell adhesion. The kinetic parameters for the substrate hydrolysis were determined through Michaelis-Menten analysis. Substrate degradation was followed by fluorescamin reaction. In a subsequent work, the rate of enzymatic gel degradation was monitored fluorimetrically by quantifying the amount of released dansylated oligopeptide from a didansyl-L-lysine-tagged protease-sensitive oligopeptide (Seliktar et al *J. Biomed. Mater. Res. A*. 2004, 68, 706-716 (2004)).

The use of protein cross-linked hydrogels in such methods has also presented problems in that the sensitivities of the system are low and the detection systems do not display a high level of specificity for proteases. This is a particular problem when the detection of a protease of clinical relevance has to be detected in a sample in order to diagnose a disease condition where sensitivity and specificity are important.

There is therefore a need for a detection method which overcomes these problems. It has now been found that a method for the detection of a protease can be advantageously carried out using a system based on thin film degradation which provides not only improved sensitivities but also high specificity for the enzyme target. Such improved methods therefore also find application in methods of diagnosing disease conditions where such diagnosis was not previously possible and/or reliable.

According to a first aspect of the invention, there is provided a method for the detection of a protease, comprising
(i) contacting a sample to be assayed with a detection means comprising a substrate partially coated with a film of a synthetic polymeric matrix
(ii) measuring a signal output of said detection means
wherein the synthetic polymeric matrix comprises a peptide comprising up to 20 amino acids.

The synthetic polymeric matrix is suitably a hydrogel cross-linked with a cross linker part of which is a peptide comprising up to 20 amino acids. Alternatively the synthetic polymeric matrix is a polymer that has been synthesised using a peptide comprising up to 20 amino acids as a polymerisable monomer. In this case the peptide and therefore the site cleaved by the protease to be detected would be an integral part of the backbone of the polymer. The polymer can be linear or branched or a network.

The synthetic polymeric matrix is suitably in the form of a polymer and at least partially coats the surface of the substrate. For example, if the substrate is substantially planar then the polymer coating layer may be applied to one of the sides of the substantially planar substrate.

The substrate may be an inert material such as a piezoelectric material, for example piezoelectric quartz, optionally partially coated with metal, metallised glass, a carbon electrode or a pair of carbon electrodes printed onto a plastic substrate, an electrode, a capacitor, or a transducer.

Where the substrate is a piezoelectric material, the detection means may suitably be a quartz crystal microbalance or a surface acoustic wave device and the signal may be measured by monitoring changes in the mass of the polymer coating layer which are reflected by changes in the resonance frequency of the quartz crystal.

Alternatively, the detection means may be a metallised inert material, such as a metallised glass material suitably in the form of a slide. The metal may suitably be an inert metal such as gold, platinum, silver etc. For example, a gold or platinum-coated glass slide. The signal output may be measured by monitoring changes in the refractive index of the polymer using a laser, for example a Helium-Neon laser (He—Ne laser). The signal may therefore be measured by detecting changes in the polymer layer using surface plasmon resonance.

The output signal can also be measured by detecting changes in the polymer layer by ellipsometry techniques. Such techniques may also utilise a laser as a light source, for example a He—Ne laser.

Another suitable method of detecting signal output which measures changes in the polymer layer is electrochemical impedance spectroscopy or impedance measurements at a single frequency. In one such embodiment, the substrate material is an electrode coated by the polymer coating layer in which the electrode is part of an electrode pair. The counter electrode is uncoated and placed adjacent or opposite to the coated electrode and measurements of the impedance of a surrounding electrolyte solution and the polymer layer can be taken. In an alternative arrangement, the polymer coating can be applied to interdigitated electrodes, in which case the impedance measurement depends on the impedance of the polymer film and the electrode/polymer film interface. Interdigitated electrodes may be advantageous since polymer film coatings with an impedance significantly larger or significantly smaller than that of the surrounding electrolyte can be detected. In some embodiments, both impedance spectroscopy and quartz crystal measurements can be taken together in appropriately constructed systems.

Other possible detection systems include those in which the signal is measured by detecting changes in the polymer layer using capacitance measurements. If the substrate is a transducer, suitably the transducer is an electrochemical transducer, an optical transducer or a capacitor.

The hydrogel may generally comprise any convenient polymeric material which permits incorporation of short peptide sequences as described herein. The polymeric material can be synthetic or naturally-occurring. Suitable examples of polymers for use in the invention include but are not limited to polyvinylpyrrolidone, acrylamide, and polymers formed from acrylic and methacrylic monomers, polyethylene glycol, polyvinylalcohol, polyethylene glycol acrylate, ethylene glycol methyl ether acrylate, dendrimers, poly(ethylene oxide) (PEO) and dextran. The hydrogel may be cross-linked with such short peptide sequences which may comprise up to 20 amino acid residues. Typically, when the polymer is dextran it is oxidised prior to cross-linking with the peptides. When the polymer is dextran, cross-linking is typically carried out using a condensation reaction.

The dendrimers are typically commercially available amino-terminated dendrimers, and are typically cross-linked using a diacrylated peptide via Michael addition reactions. Poly(ethylene oxide) is typically cross-linked using the unmodified peptide. The poly(ethylene oxide) is typically activated, for example, by activation of functional groups to render them electrophilic, for example, by conversion of alcohol groups to tosylate, mesylate, halide etc. Such electrophilic functional groups will then react with the amine functional groups of the cross-linking peptides.

The electrodes of the present invention may be composed of noble metals or carbon. Noble metals include metals such as gold, silver and platinum, or alloys thereof, which display resistance to corrosion or oxidation. Preferably the electrode is gold. Typically, the gold is deposited by thermal evaporation onto a chromium coated glass slide. The thickness of the gold coating may vary considerably, but is usually between 20 and 100 nm. Preferably, the thickness of the gold coating is between 45 and 80 nm.

The substrate is suitably coated with a thin film of the hydrogel polymer material. The film may range from monolayers to several hundred nm thick. Preferably, the film is from about 2 to 1000 nm thick, suitably from 5 to 100 nm thick. More preferably, the film is 10 to 100 nm thick. Typically, the films are deposited on the surface of the substrate by spin-coating, spray coating, drop-coating or printing using a solution of reactants in an appropriate solvent (for example dimethylformamide, acetonitrile, water, chloroform or acetone) and formation of the polymer by radical polymerisation in the presence of a suitable initiator. The biodegradable films degrade rapidly under the catalytic action of a specific protease directed to the polymer used to coat the substrate.

The preferred coatings in the present application degrade within a matter of seconds or minutes in the presence of a single enzyme, thereby leading to a fast sensor response. In contrast, up to now, most biodegradable materials described in the literature are reported to degrade over the course of several hours or days (Arabuli et al *Macromolecular Chemistry and Physics,* 195, 2279-2289 (1994); Brondsted et al *Stp Pharma Sciences,* 5, 60-64 (1995)). Thus the present invention provides a sensor displaying short response times.

The hydrogel polymer films may be deposited onto the substrate surface of known thickness and may then be dissolved (degraded) directly due to the action of a protease on the polymer film. The enzyme can be in close proximity to or inside the polymer film. The films proposed in the present sensor system are very homogeneous and respond in a matter of minutes due to enzyme amplification, thus resulting in higher sensitivities and lower limits of detection. Coating degradation may be followed using surface plasmon resonance (SPR), quartz crystal microbalance (QCM) or ellipsometry where the rate of dissolution of the film is directly related to the concentration or activity of enzyme.

The signals measured by the methods of the present invention may be produced in response to a reduction of the polymer layer on the substrate, either in terms of the area of the substrate covered by the polymer layer, or in terms of the depth of the polymer layer. The signal may also be produced in response to the quality of the polymer layer, for example in terms of pore formation, swelling and/or delamination.

In preferred methods of the invention quartz crystal microbalance (QCM), surface plasmon resonance (SPR) and ellipsometry may be used to determine properties of surfaces and thin films. All of these techniques have been applied successfully to biosensing, especially to monitoring of direct binding events between antigens and antibodies (Rickert et al *Biosensors and Bioelectronics* Toyama et al *Sensors and Actuators B-Chemical,* 52, 65-71 (1998): Arwin, H., *Thin Solid Films* 764-774 (1998)). Direct binding produces changes to the electrode surfaces that are more indicative of a porous layer, resulting in very small changes being observed.

Electrochemical impedance spectroscopy provides information about film properties such as incomplete coverage, pore formation, swelling and delamination. The initial film quality and film degradation of the present invention may be studied using electrochemical impedance spectroscopy over a frequency range from 0.1 mHz to 100 kHz. In addition to the information extracted from impedance spectroscopy, impedance measurements at quartz crystals provide data such as changes in mass and the visco-elastic properties of the films during degradation. In order to extract this information, the quartz crystal impedance spectra may be fitted to the equivalent circuit of a coated quartz crystal given in Auge et al *Sensors and Actuators B-Chemical,* 19, 518-522 (1994). Typically, impedance measurements are performed at polymer coated quartz crystals at a number of frequencies close to the resonance frequency of 10 MHz.

The peptide cross-linker molecule comprises up 20 amino acid residues. Suitably, the length of the peptide may be up to 18 residues, 17 residues, 16 residues, 15 residues, 14 residues, 13 residues, 12 residues, 11 residues, 10 residues, 9 residues, 8, residues, 7 residues, 6 residues, 5 residues, 4 residues or up to 3 residues.

The peptide may be composed of any one of the following naturally occurring amino acid residues in any combination or number as may be required for the protease enzyme to cleave the sequence:

Alanine, Arginine, Asparagine, Aspartic acid, Asparagine, Cysteine, Glutamine, Glutamic acid, Glycine, Histidine, Isoleucine, Leucine, Lysine, Methionine, Phenylalanine, Proline, Serine, Threonine, Tryptophan, Tyrosine, Valine.

The above amino acids may be represented by the short 3-letter code as:

Ala, Arg, Asn, Asp, Cys, Gln, Glu, Gly, H is, Ile, Leu, Lys, Met, Phe, Pro, Ser, Thr, Trp, Tyr, Val or alternatively, by the one-letter code as:

A,R,N,D,C,Q,E,G,H,I,L,K,M,F,P,S,T,W,Y,V

Where Asx or B is used to denote Asparagine or Aspartic acid, Glx or Z is used to denote Glutamine or Glutamic acid, and X is any amino acid residue.

The sequence of the peptide sequence may be chosen to reflect the specificity of the protease enzyme to be detected or it may be a variant of the natural cleavage site and/or binding site.

An example of a variant sequence is a sequence in which one or more residues have been altered or modified, or a sequence in which there has been a substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions. Amino acid deletions or insertions may also be made relative to the amino acid sequence of the peptide cleavage site and/or binding sequence of the protease referred to above. Thus, for example, amino acids which do not have a substantial effect on the activity of the protease, or at least which do not eliminate such activity, may be deleted.

Amino acid insertions relative to the sequence of the peptide can also be made. This may be done to alter the properties of the peptide (e.g. to enhance binding or specificity of cleavage).

Amino acid changes relative to the sequence given in a) above can be made using any suitable technique e.g. by using site-directed mutagenesis for recombinantly expressed peptides.

It should be appreciated that amino acid substitutions or insertions within the scope of the present invention can be made using naturally occurring or non-naturally occurring amino acids. Whether or not natural or synthetic amino acids are used, either D- or L-amino acids may be used. Seleno analogues of cysteine or methionine may be used.

The proteases that can be detected according to a method of the invention, include but are not limited to serine proteases, matrix metalloproteinases, and gingipain proteases.

Serine proteases are also known as serine endopeptidases. The enzymes currently know to fall in this group are Chymotrypsin, Chymotrypsin C, Metridin, Trypsin, Thrombin, Coagulation factor Xa, Plasmin, Enteropeptidase, Acrosin, Alpha-lytic endopeptidase, Glutamyl endopeptidase, Cathepsin G, Coagulation factor VIIa, Coagulation factor IXa, Cucumisin, Prolyl oligopeptidase, Coagulation factor XIa, Brachyurin, Plasma kallikrein, Tissue kallikrein, Pancreatic elastase, Leukocyte elastase, Neutrophil elastase, Coagulation factor XIIa, Chymase, Complement subcomponent C1r, Complement subcomponent C1s, Classical complement pathway C3/C5 convertase, Complement factor I, Complement factor D, Alternate complement pathway C3/C5 convertase, Cerevisin, Hypodermin C, Lysyl endopeptidase, Endopeptidase La, Gamma-renin, Venombin AB, Leucyl endopeptidase, Tryptase, Scutelarin, Kexin, Subtilisin, Oryzin, Endopeptidase K, Thermomycolin, Thermitase, Endopeptidase So, T-plasminogen activator, Protein C (activated), Pancreatic endopeptidase E, Pancreatic elastase II, IgA-specific serine endopeptidase, U-plasminogen activator, Venombin A, Furin, Myeloblastin, Semenogelase, Granzyme A, Granzyme B, Streptogrisin A, Streptogrisin B, Glutamyl endopeptidase II, Oligopeptidase B, Limulus clotting factor C, Limulus clotting factor B, Limulus clotting enzyme, Omptin, Repressor lexA, Signal peptidase I, Togavirin, Flavivirin, Endopeptidase Clp., Proprotein convertase 1, Proprotein convertase 2, Snake venom factor V activator, Lactocepin, Assemblin, Hepacivirin, Spermosin, Pseudomonalisin, Xanthomonalisin, C-terminal processing peptidase, and Physarolisin.

The best known examples of serine proteases include trypsin, chymotrypsin, cathepsin G, subtilisin and elastase (for example, human neutrophil elastase).

Chymotrypsin is responsible for cleaving peptide bonds flanked with bulky hydrophobic amino acid residues. Preferred residues include phenylalanine, tryptophan, and tyrosine, which fit into a hydrophobic pocket in the protein folds of the enzyme. Trypsin is responsible for cleaving peptide bonds flanked with positively charged amino acid residues. The hydrophobic pocket in the enzyme has an aspartic acid residue at the back of the pocket. This can then interact with positively charged residues such as arginine and lysine. Elastase is responsible for cleaving peptide bonds flanked with small neutral amino acid residues, such as alanine, glycine and valine. The hydrophobic pocket is lined with valine and threonine thus it can accommodate these smaller amino acid residues.

In the methods of the present invention, the action of the protease on the peptide cross-linked hydrogel is to degrade the hydrogel. The term degradation is used in its conventional sense, i.e., a chemical reaction in which a compound is converted, or decomposes in some way, to give a simpler compound, for example, by dissolution. In the context of the present invention, such degradation of the cross-linked hydrogel polymer describes the process of dissolving or reducing the cross-link density of the polymer.

Matrix metalloproteinases (MMP's) are zinc-dependent endopeptidases, other family members are ADAMs, Serralysins, Astacins. The MMP's belong to a larger family of proteases, the Metzincin superfamily. Collectively such enzymes are capable of degrading all kinds of extracellular matrix proteins, but also can process a number of bioactive molecules. They are known to be involved in cleavage of cell surface receptors, release of apoptotic ligands, and chemokine in/activation.

The main MMP's known to date include the enzymes specific for collagen known as "Collagenases". These MMPs are capable of degrading triple-helical fibrillar collagens into distinctive ¾ and ¼ fragments. These collagens are the major components of bone and cartilage, and MMPs are the only known mammalian enzymes capable of degrading them. The collagenases are: MMP-1, MMP-8, MMP-13, and MMP-18. MMP-14 (MT1-MMP) has also been shown to cleave fibrillar collagen, and there is evidence that MMP-2 is capable of collagenolysis. Another group of MMP's is the "Stromelysins" which display a broad ability to cleave extracellular matrix proteins but are unable to cleave the triple-helical fibrillar collagens. The group includes: MMP-3, MMP-10 and MMP-11. MMP-11 shows more similarity to the MT-MMPs, is convertase-activatable and is secreted therefore usually associated to convertase-activatable MMPs.

Other MMP's include Metalloelastase (MMP-12) MMP-19 Enamelysin (MMP-20) MMP-27 (MMP-22, C-MMP), the "Matrylysins" which include Matrylysin (MMP-7) Matrylysin-2 (MMP-26), and the "Gelatinases". The main substrates of the gelatinase MMPs are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (expressed in most tissues) and MMP-9 (predominantly found in neutrophils).

There are also the "Convertase-activatable MMPs" and the secreted MMP's including Stromelysin (MMP-11) MMP-21 (X-MMP) Epilysin (MMP-28). The Membrane Bound MMPs include: the type-II transmembrane cysteine array MMP-23; the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively). All 6 MT-MMPs have a furin cleavage site in the pro-peptide, which is a feature also shared by MMP-11. Other known MMP's include MMP-23A MMP-23B.

Gingipain proteases include arg-gingipain and lys-gingipain.

For example, the peptide may be between 3 to 9 amino acid residues in length, for example 7 or 9 amino acid residues in length. Preferred sequences include, but are not limited to:

```
Ala-Pro-Glu-Glu-Iso-Met-Asp-Arg-Lys (APEEIMDRK)
(SEQ ID NO: 1)

Ala-Ala-Pro-Val-Ala-Ala-Lys (AAPVAAK)
(SEQ ID NO: 2)

Ala-Pro-Glu-Glu-Iso-Met-Asp-Arg-Glu (APEEIMDRQ)
(SEQ ID NO: 3)

Ala-Pro-Glu-Glu-Iso-Met-Asp-Arg (APEEIMDR)
(SEQ ID NO: 4)

Ala-Ala-Pro-Val (AAPV) (SEQ ID NO: 5)

Ala-Ala-Pro-Phe (AAPF) (SEQ ID NO: 6)

Ala-Ala-Pro-Phe-Phe-Lys (AAPFFK)
(SEQ ID NO: 7)
```

-continued

Gly-Gly-Arg (GGR) (SEQ ID NO: 8)

Gly-Pro-Gln-Gly-Ile-Trp-Gly-Gln (GPQGIWGQ) (SEQ ID NO: 9)

Phe-Ala-Ala-Phe-Phe (FAAFF) (SEQ ID NO: 10)

The peptides Ala-Pro-Glu-Glu-Iso-Met-Asp-Arg-Lys (SEQ ID NO:1), Ala-Ala-Pro-Val-Ala-Ala-Lys (SEQ ID NO:2), Ala-Pro-Glu-Glu-Iso-Met-Asp-Arg-Glu (SEQ ID NO:3), Ala-Pro-Glu-Glu-Iso-Met-Asp-Arg (SEQ ID NO:4) and Ala-Ala-Pro-Val (SEQ ID NO:5) are all preferentially cleaved by human neutrophil elastase.

Ala-Ala-Pro-Phe (SEQ ID NO:6) and Ala-Ala-Pro-Phe-Phe-Lys (SEQ ID NO:7) are preferentially degraded by cathepsin-G, Gly-Gly-Arg (SEQ ID NO:8) is cleaved by arg-gingipain, Gly-Pro-Gln-Gly-Ile-Trp-Gly-Gln (SEQ ID NO:9) is a preferred substrate for MMP8 and Phe-Ala-Ala-Phe-Phe (SEQ ID NO:10) is a preferred substrate for subtilisin.

In some embodiments, the peptide contains a lysine residue at the C-terminus to enable the peptide to cross-link the synthetic polymeric matrix via its amine terminal group.

The peptides may be optionally amidated ($NH_2$) at the C-terminus and may also comprise succinate residues at the N-terminus. Other C-terminus and N-terminus linker groups may also be included as desired.

Preferably the samples are in the form of an aqueous sample, or a biological fluid, for example, blood, urine, serum, plasma or saliva.

Accordingly, the method of the invention does not require the presence of a detectable label such as a fluorescent or radioactive label bound to the peptide.

According to a second aspect of the present invention, there is provided apparatus for detection of a protease according to a method of the first aspect of the invention, in which the apparatus comprises a detection means comprising a substrate partially coated with a film of a cross-linked hydrogel, wherein said hydrogel is cross-linked with a peptide comprising up to 20 amino acids According to a third aspect of the present invention, there is provided a method according to the first aspect for the diagnosis of an inflammatory disease or condition. Such a method may therefore suitably comprise assaying a patient sample for the presence of a protease, where the presence of protease may include the detection of raised levels of protease above levels of protease in a control patient sample (where the patient is not diseased).

Apparatus to perform such a diagnosis may be as described above. The apparatus may be constructed in a disposable format, for example, based on an "dip-stick" format where a disposable test strip is used to insert the sample for analysis into contact with an electrode.

It is also envisaged that the methods of the present invention may find use in enhanced competitive-binding assays or enzyme-linked immunoassays where the antibody used for detection is coupled to a protease, such that the protease provides the indication of the level of successful antibody/antigen binding (rather than the usual enzymes such as Horseradish Peroxidase or Alkaline phosphatase). A schematic is shown in FIG. 13.

For example the assay may employ binding pairs such as avidin/biotin, antibody/antigen, haptens and nucleic acid (DNA and RNA). Generally, when the binding pair is antibody/antigen the assay is referred to as an immunoassay. Other biosubstances capable of molecular recognition include lectins for saccharides, hormone receptors for hormones and drug receptors for drugs and active drug metabolites. In a preferred aspect, the method of the present invention is used for performing an immunoassay.

Typically, in enzyme immunoassays, an enzyme is used as a label or marker which is bound to one member of the antigen-antibody pair identical to that in the sample to be measured. The enzyme bound antigen/antibody then competes with the sample antigen/antibody for the binding site on a limited supply of its complement antibody/antigen. In the present invention, the marker is a protease enzyme.

Classical methods for immunoassay include: (i) a capture antibody on a solid phase, such as a plastic microtitre plate, exposure to the biological sample to attach the antigen of interest, washing and then exposure to a second labelled antibody. The label on the antibody may be an enzyme for example.

Further washing is followed by detection of the label (and hence the amount of antigen in the original sample). This is known as a sandwich assay or two-site assay. (ii) a capture antibody on the solid phase followed by exposure to the biological sample containing antigen and an added amount of labelled antigen. Labelled and unlabelled antigen compete on the solid phase for the antibody sites. The amount of label revealed after washing is inversely proportional to the amount of true antigen in the biological sample. This is known as a competitive assay.

The concept of integrating enzyme and immunoassay techniques into the sensor devices disclosed in the present invention thus offers the prospect of reagent-less analysis with little or no sample preparation. The major advantage of this approach for medical use is ease of operation, thereby allowing deployment of sensors in decentralised laboratories and facilitating a more rapid return of clinical information. The net benefit is an earlier institution of appropriate therapy.

In a preferred embodiment an immunosensor can be produced where the sample flows through a series of zones. The first of these is a blood separation membrane, which removes the cellular component. In the next zone, the capture antibody or antigen is immobilised on a substrate such as nitrocellulose membrane or polystyrene. A sample is introduced containing the analyte to be measured and mixes with an enzyme/antigen or enzyme/antibody conjugate. The mixture of analyte and conjugate will then flow over the capture antibody or antigen. Both conjugate and analyte compete for the binding sites. Flow through the capture membrane will remove some of the enzyme-analyte conjugate in a competitive manner. In the next zone, the unbound complex reaches the biodegradable polymer and causes it to degrade. The rate of polymer dissolution is directly proportional to the amount of analyte in the sample. The immunoassay can be set up in the competitive or sandwich assay format.

Further aspects of the invention are found in uses of a method of the invention for the detection of bacterial infection, for the measurement of protease activity in a detergent composition, for the screening of protease inhibitors, and for monitoring of exposure of an individual to a protease enzyme in the environment.

For example, protease inhibitors prevent T-cells that have been infected with HIV from producing new copies of the virus. When new viral particles break off from an infected cell, protease cuts long protein strands into the parts needed to assemble a mature virus. When protease activity is blocked, the new viral particles cannot mature. The methods of the present application can therefore be used to measure the effectiveness of protease inhibitors by measuring free protease activity. Low molecular weight substrates that are used in standard assays are frequently cleaved by inhibited enzyme and can therefore not be used as a true indication of free protease activity.

The methods of the present invention will also permit distinction between bacterial and host proteases providing an indicator for bacterial infection. Early detection of bacterial infection would have enormous benefits in many different applications. There are two broad application areas for this technology—wound management (both clinical and domestic situations), and detecting infection in food manufacture and retailing. In wound management there are delays of several days in detecting infection e.g. even badly burned patients rely on swabs being taken and cultures being grown—in such patients pockets of bacterial infection can rapidly lead to sepsis which early detection could have prevented. In food retailing early detection of bacterial contamination in food would assist retailer and consumer alike.

Subtilisin-like bacterial proteases are used in large amounts by detergent manufacturers and in the brewing industry. They are implicated as major factor in occupational asthma and allergic rhinitis and there is significant concern about occupational exposure to this agent.

Modern detergents for washing clothes and other materials often contain protease enzymes such as subtilisin, in addition to the surfactant molecules present. Sensors according to the methods of the present invention could also be used to measure protease activities under conditions found during the wash process where detergent compositions are used. The benefits of a protease sensor would be twofold. The sensor could be integrated into an automated system for testing new detergent formulations reducing the development time of washing powders considerably. Furthermore, a protease biosensor could be used to monitor protease activities throughout the wash in order to optimise the wash process and dosage of detergent.

Preferred features for the second and subsequent aspects of the invention are as for the first aspect mutatis mutandis.

The present invention will now be further described by way of illustration with reference to the following examples and drawings which are not to be construed as being limiting on the invention. In the following examples, reference is made to a number of Figures in which.

Figure 5:
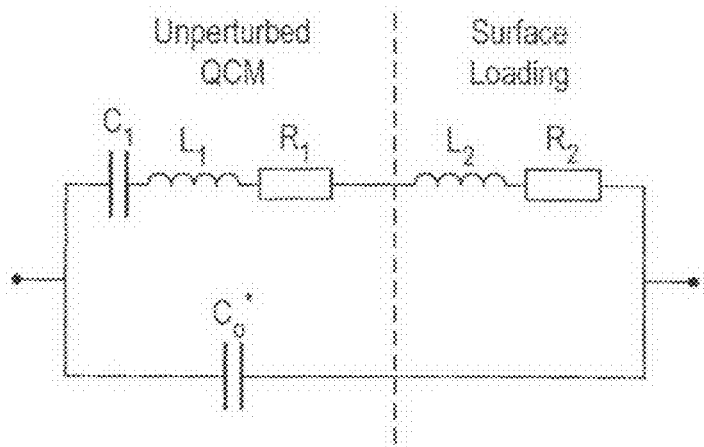

FIG. 5 shows a Butterworth-Van Dyke equivalent circuit for a QCM resonator with surface loading. The surface loading arises from the presence of a coating and from the coating in contact with a liquid. The surface loading is represented by the motional inductance $L_2$ and resistance $R_2$.

Figure 6:
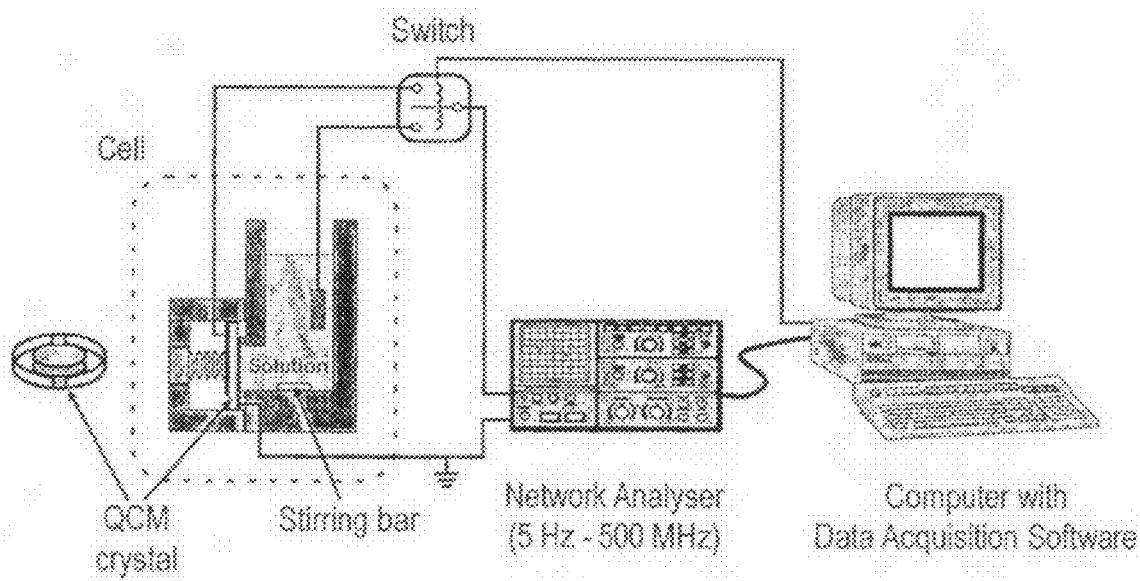

FIG. 6 shows an experimental set-up for combined quartz crystal admittance measurements and impedance spectroscopy (A. Sabot Sr. S. Krause *Anal Chem.* 74, 3304-3311 (2002)).

Figure 7:
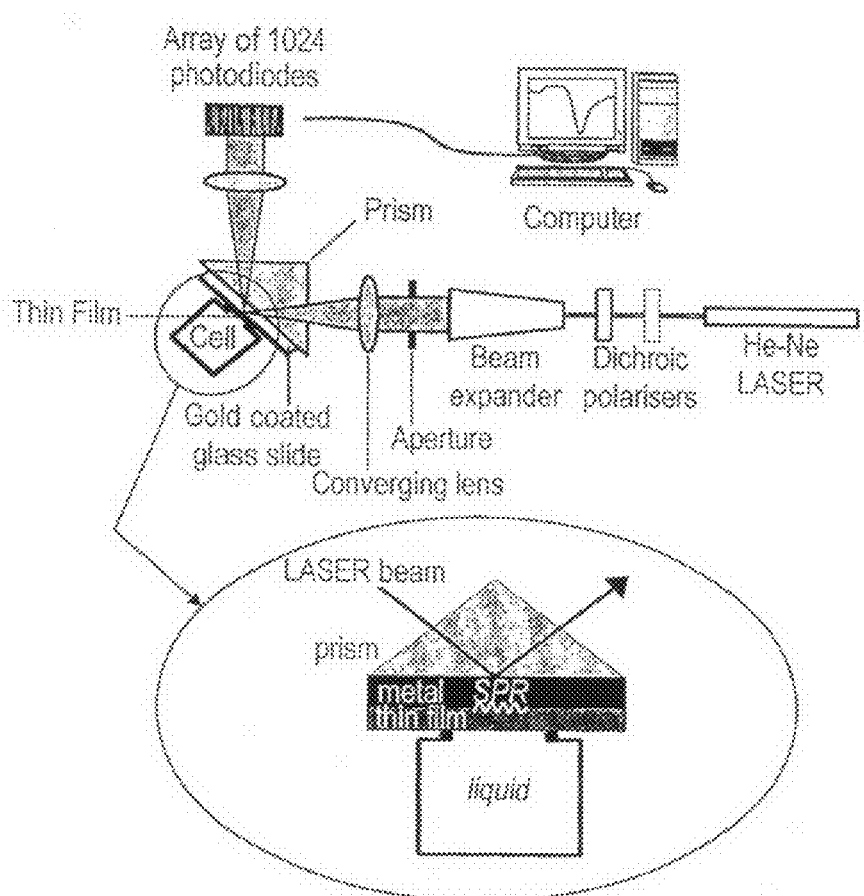

FIG. 7 shows a schematic of a SPR set-up for monitoring the degradation of a thin film hydrogel polymer (Sumner et al *Anal. Chem.* 72, 5225-5232 (2000)).

Figure 8:
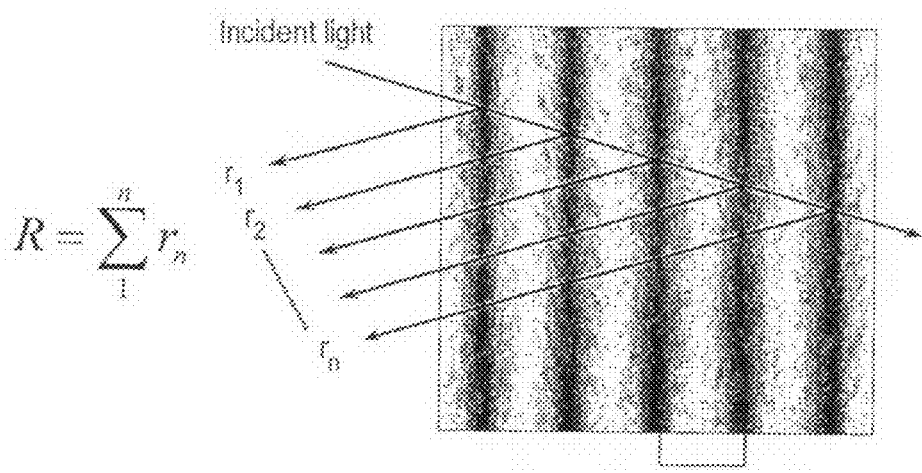

FIG. 8 shows the general principle of a holographic sensor.

Figure 9:
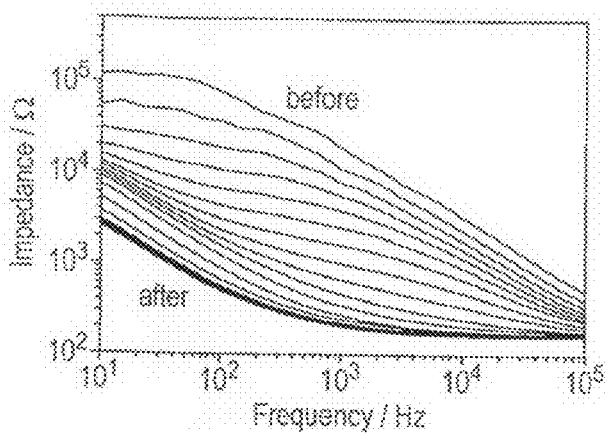

FIG. 9 shows impedance spectra measured during degradation (one spectrum every minute) from A. Sabot & S. Krause (*Anal. Biochem,* 74 3304-3311 (2002)).

Figure 10:
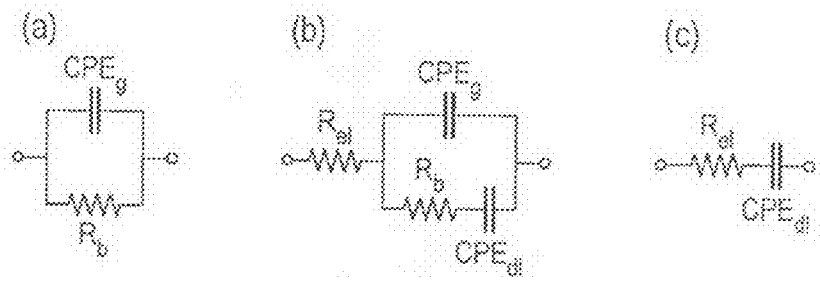

FIG. 10 shows equivalent circuits used to describe the behaviour of Eudragit S100 films during degradation from A. Sabot & S. Krause (*Anal. Biochem.* 74 3304-3311 (2002)).

Figure 11:
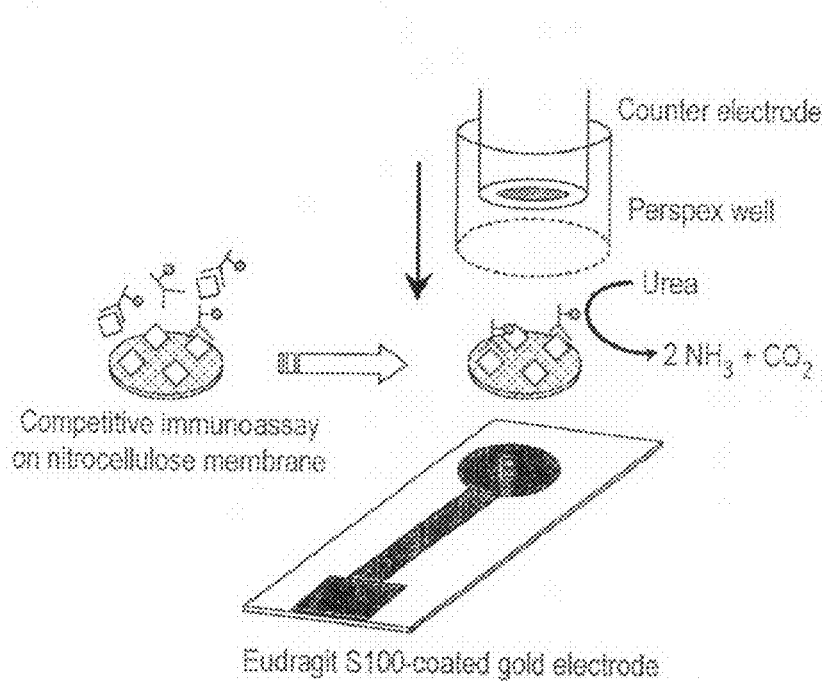

FIG. 11 shows the schematic layout of an immunosensor for human IgG based on a competitive immunoassay format.

Figure 12:
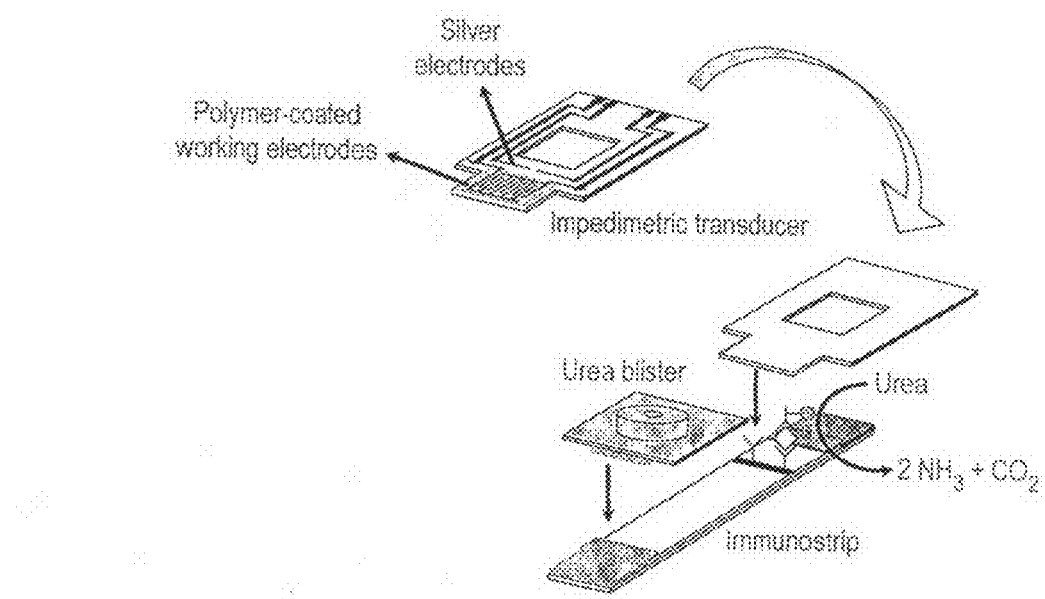

FIG. 12 shows the schematic layout of an immunosensor for PSA based on a non-competitive lateral flow immunoassay format.

Figure 13:
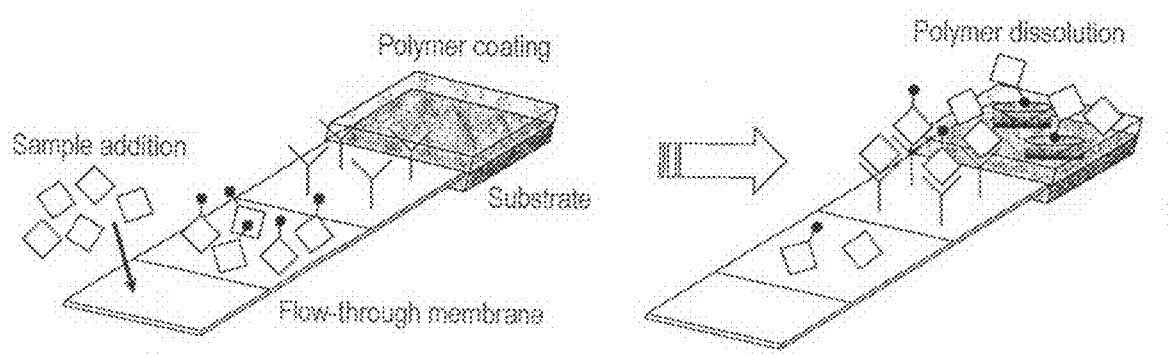

FIG. 13 shows the schematic layout of an immunosensor device based on a competitive flow through immunoassay format.

Figure 14:
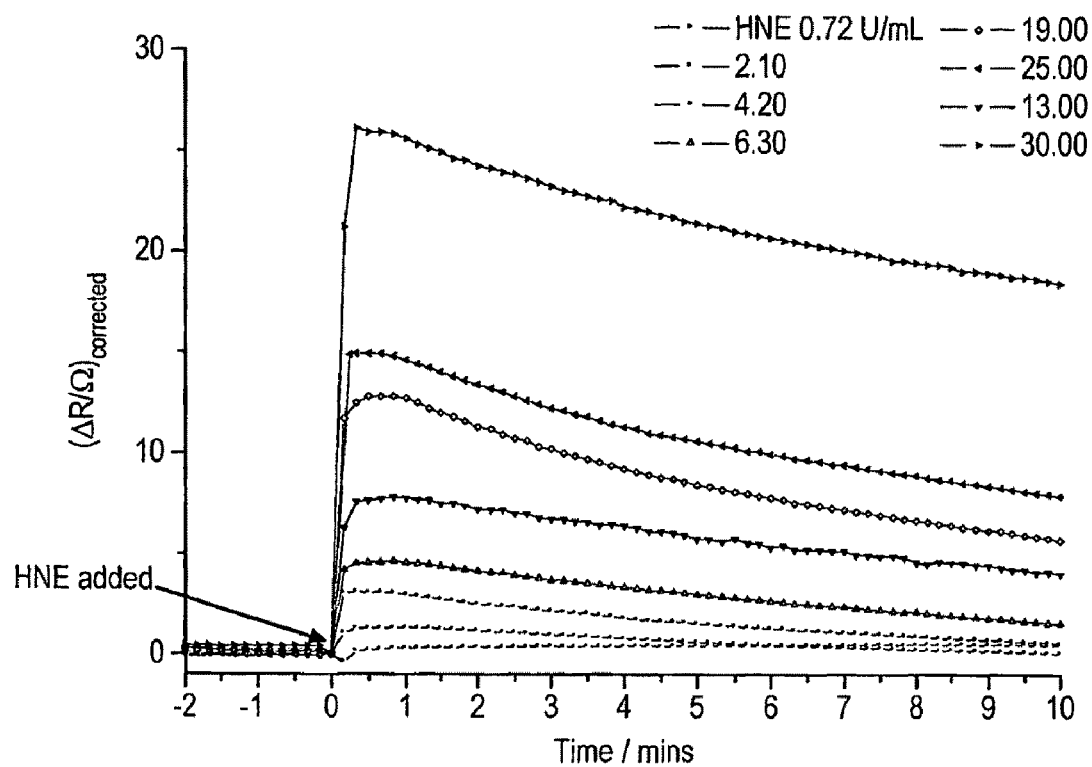

FIG. 14 shows the change in resistive component with time at different Human Neutrophil Elastase (HNE) concentrations.

Figure 15:
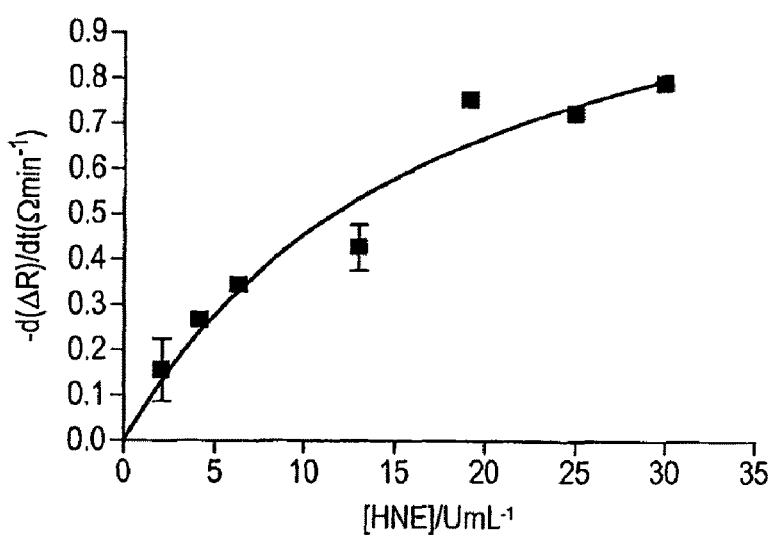

FIG. 15 shows a calibration plot for rate of degradation of peptide cross-linked hydrogel films based on changes in motional resistance with HNE concentration.

Figure 16:
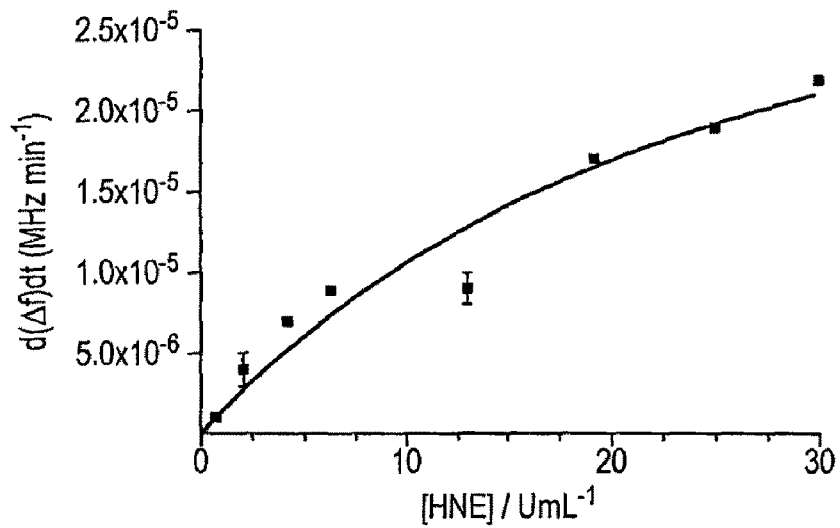

FIG. 16 shows dependence of rate of $\Delta f$ increase ($d(\Delta f)/dt$) on HNE concentrations. The error bars for HNE 2.1 and 13.0 U mL$^{-1}$ were determined using the 95% confidence interval of 4 samples.

Figure 17:
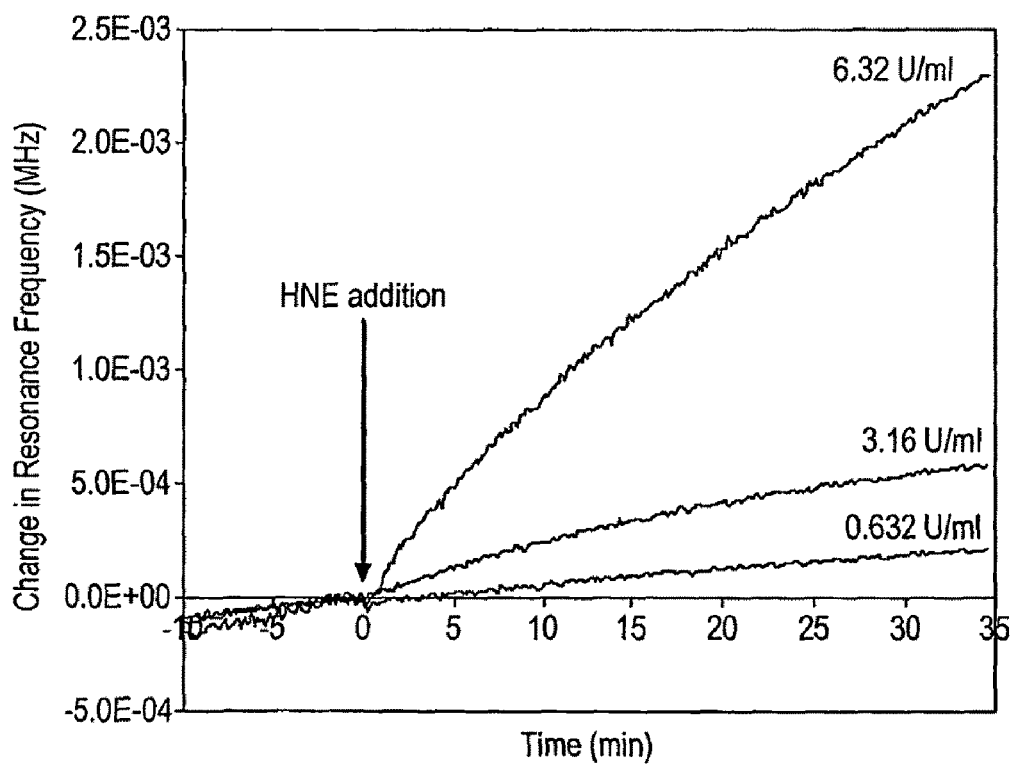

FIG. 17 shows the change in quartz crystal resonance frequency for AAPVAAK 50% cross-linked dextran hydrogel at various HNE concentrations.

Figure 18:
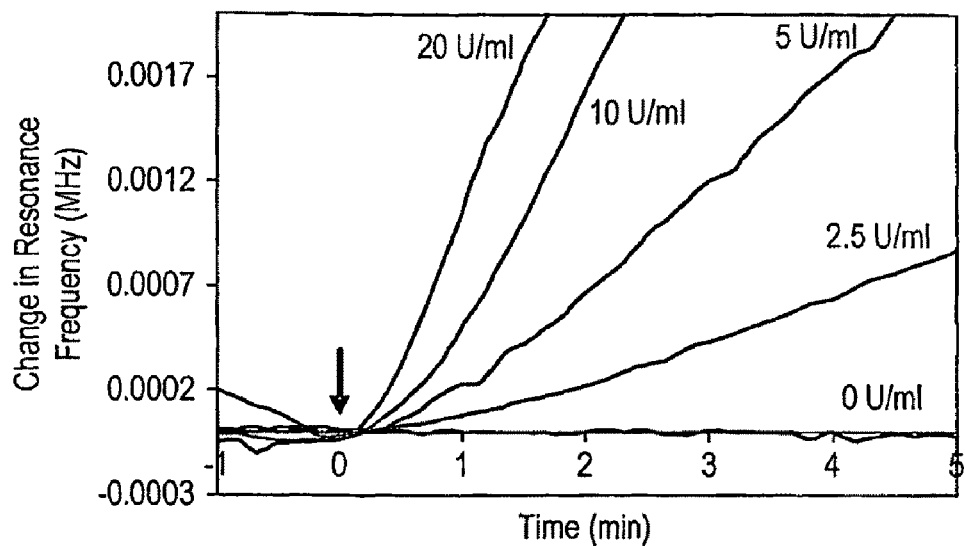

FIG. 18 shows the change in quartz crystal resonance frequency for AAPVAAK 25% cross-linked dextran hydrogel at various HNE concentrations. The arrow indicates where degradation begins.

Figure 19:
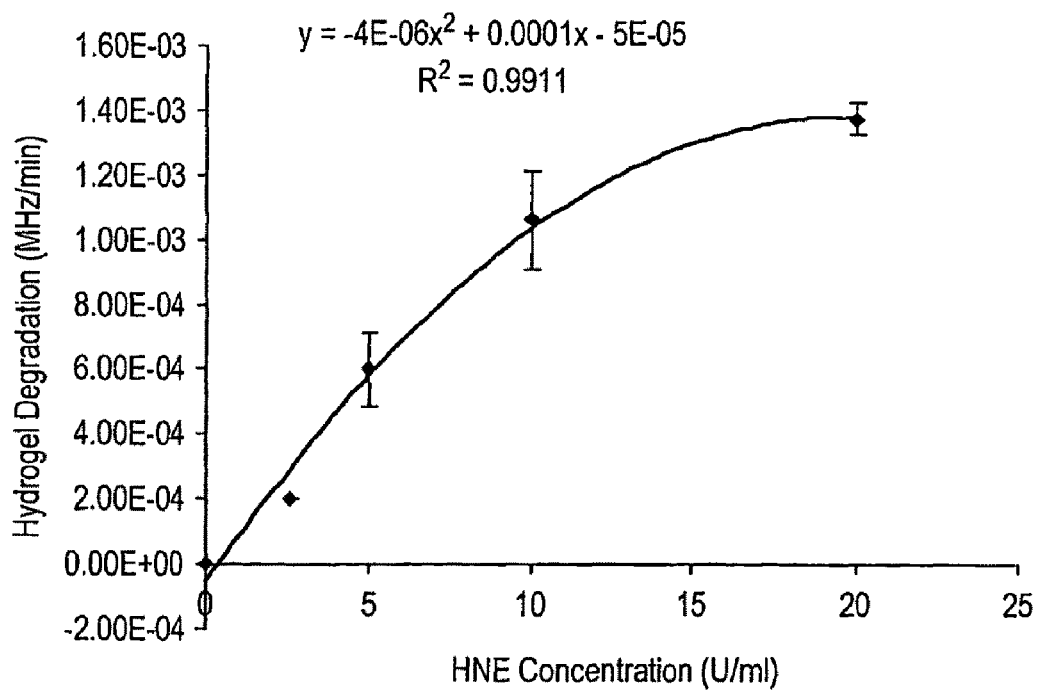

FIG. 19 shows the change in resonant frequency over time with HNE concentration.

Figure 20:
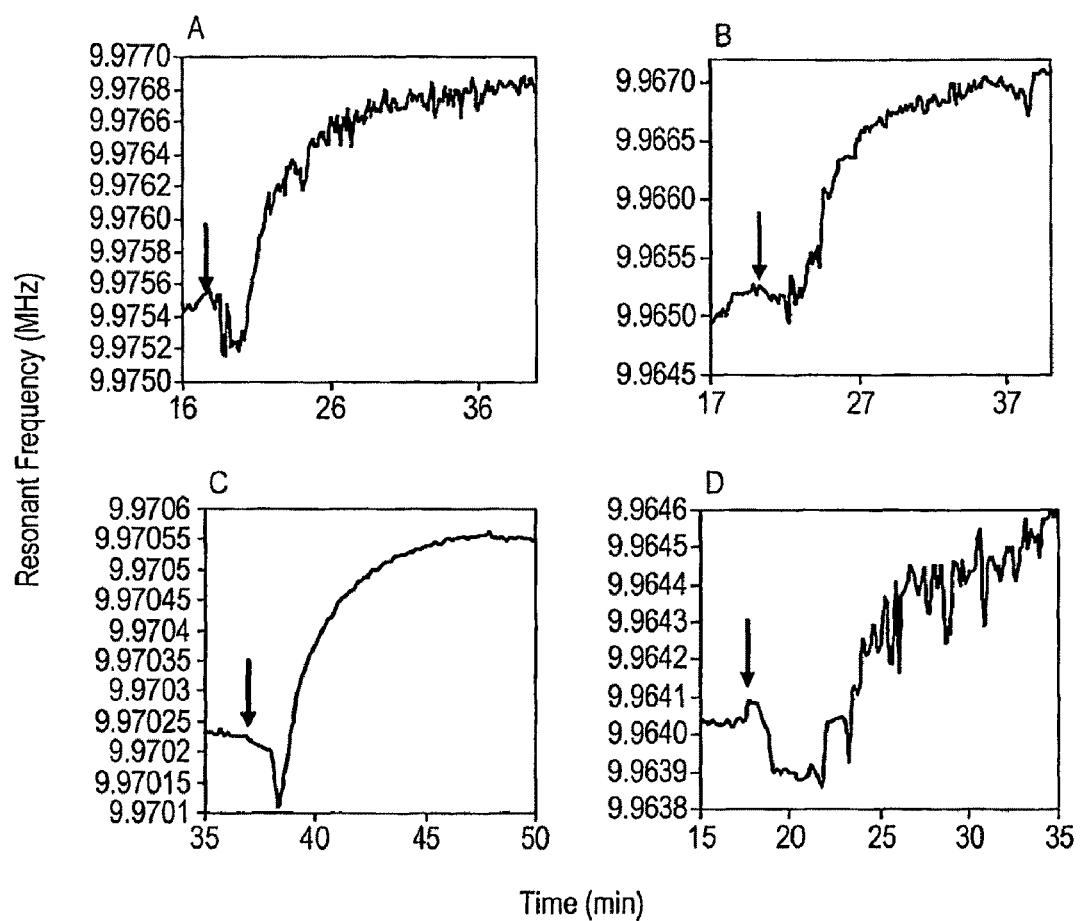

FIG. 20 shows cathepsin G degradation of AAPFFK (cross-linked dextran hydrogels batch 1 (A&B) and batch 2 (C&D). The arrow indicates when cathepsin G was added to the solution.

Figure 21:
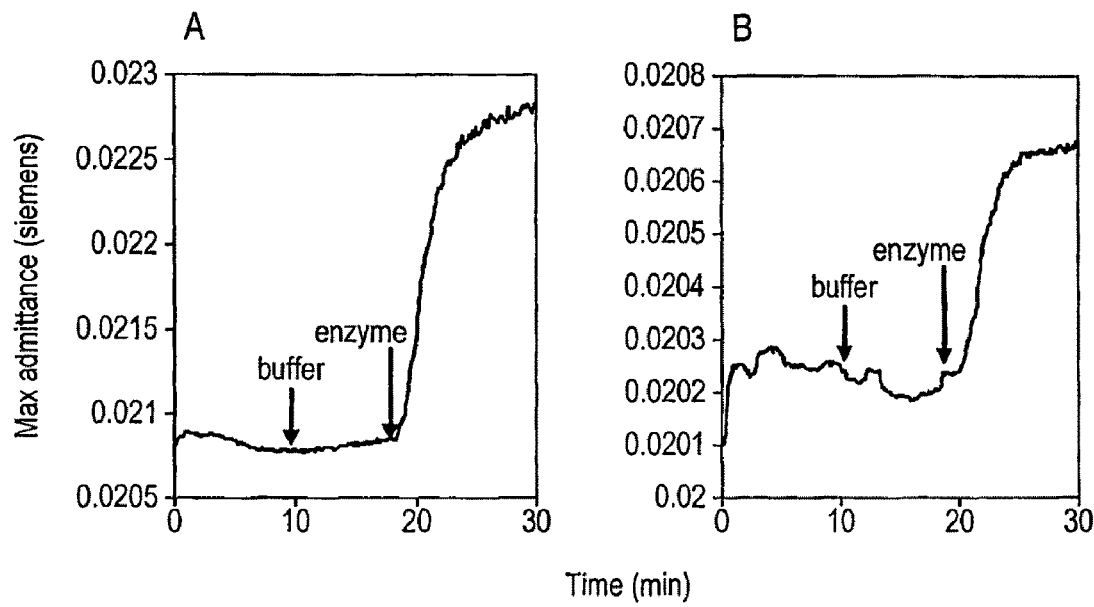

FIG. 21 shows the maximum admittance response of AAPFFK 25% cross-linked dextran hydrogels when exposed to buffer and cathepsin G. The hydrogels are A&B from batch 2.

Figure 22:
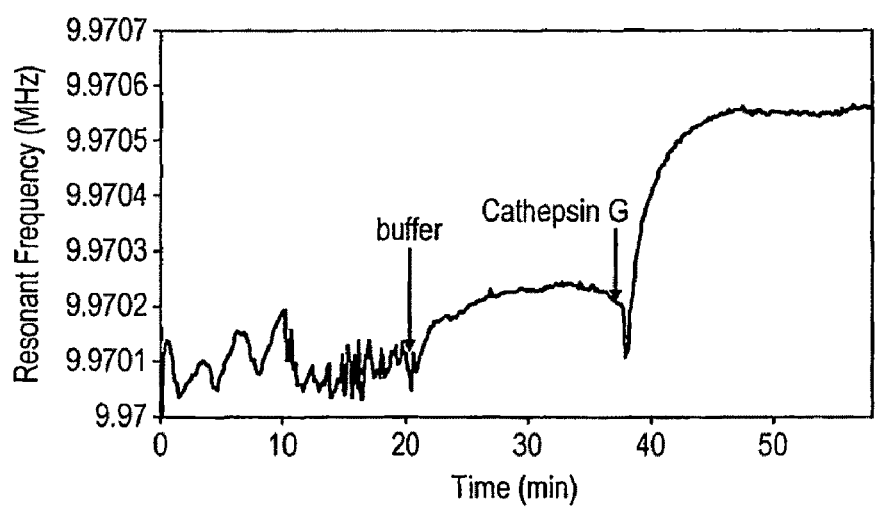

FIG. 22 shows the QCM response of AAPFFK cross-linked dextran hydrogels exposed first to buffer and then to cathepsin G.

Figure 23:
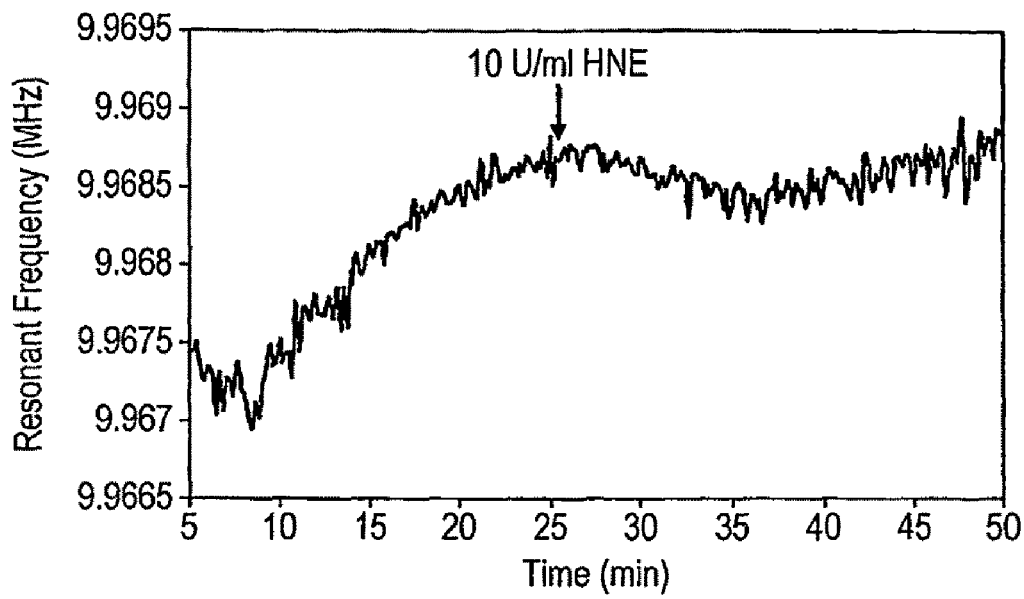

FIG. 23 shows the QCM response of AAPFFK cross-linked dextran hydrogels when exposed to HNE.

Figure 24:
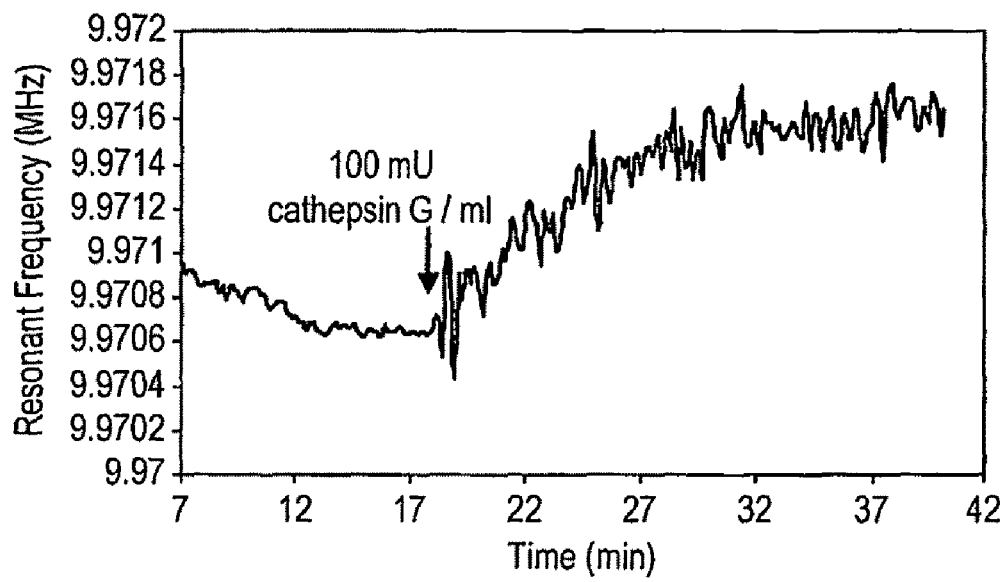

FIG. 24 shows the QCM response of AAPVAAK cross-linked dextran hydrogels when exposed to cathepsin G.

FIGS. 2 to 13 are reproduced from Krause et al "Sensors based on thin film degradation", in *"Encyclopedia of sensors"*, in press, American Scientific Publishers, ISBN: 1-58883-056-X (2005).

EXAMPLE 1

Construction of Materials and Sample Preparation

The examples reported in the present application were focused on the development of peptide hydrogel targeted for degradation by Human Neutrophil Elastase (HNE) for use in a biosensor. Quartz crystal microbalance (QCM) measurements were used to monitor the degradation processes. This technique has been used previously to study the degradation of a variety of thin polymer films. (Sabot, A.& Krause, S. *Anal. Chem.*, 74, 3304-3311 (2002)). The technique was now extended to study the properties of peptide hydrogels degradable by HNE.

1-Hydroxyundecanethiol, acrylamide (AAm), acryloyl chloride, 2,2-dimethoxy-2-phenyl-acetophenone (DMPA) and diisopropylethylamine, DIPEA were purchased from Aldrich. Organic solvents such as dimethylformamide (DMF) and N-vinyl pyrrolidinone (NVP) were also purchased from Aldrich and used as received. The peptides containing the elastase-labile sequences, Ala-Pro-Glu-Glu-Iso-Met-Asp-Arg-Lys-NH2 (APEEIMDRK) (SEQ ID NO:1) and Ala-Ala-Pro-Val-Ala-Ala-Lys-NH2 (AAPVAAK) (SEQ ID NO:2), were synthesized by Dr. A. Moir of MBBS Department, University of Sheffield.

Human neutrophil elastase, MW 25 900, from human sputum, with an activity of 875 units mg$^{-1}$ was purchased from Elastin Products (U.S.A.). Phosphate buffer pH 7.4 containing 140 mM NaCl and 10 mM KH$_2$PO$_4$ was prepared using ultra pure water, purified through a Milli-Q ion exchange system (Millipore).

Polished, gold-coated QCM crystals (10 MHz) were purchased from Elchema. Prior to film deposition, the quartz crystals were cleaned by boiling in piranha solution (7:3 v/v concentrated H$_2$SO$_4$ and 20% H$_2$O$_2$) for 15 min, rinsed thoroughly, first with deionized water, then with spectrophotometric-grade ethanol (Aldrich), and finally dried with a stream of nitrogen. All cleaned crystals were then immersed in 50 mM of 1-hydroxyundecanethiol in ethanol:water (4:1) overnight to improve the wettability of the gold surface.

Two different substrates for the enzyme HNE have been identified. The peptide chosen initially has the sequence ala-pro-glu-glu-iso-met-asp-arg-lys (APEEIMDRK) (SEQ ID NO:1). The second substrate has the sequence ala-ala-pro-val-ala-ala-lys (AAPVAAK) (SEQ ID NO:2). Both substrates were chosen based on reports by Korkmaz et al and McRae et al respectively with some modifications to suit reaction requirement (Korkmaz et al Journal of Biological Chemistry, 277, 39074-39081 (2002); Castillo et al Anal Biochem. 99, 53-64 (1979); McRae et al Biochemistry, 19, 3973-3978 (1980)).

EXAMPLE 2

Synthesis of Peptide Hydrogel

This section discusses briefly the synthesis of the elastase-sensitive peptide hydrogel.

a) Synthesis of Peptide Cross-Linker

The substrates were activated for reactions with acrylamide by capping both ends with an acryloyl group following similar procedure detailed by Hunter (Hunter et al *Chem. Eur. J*, 8, 5435-5446 (2002)) with some modifications. Briefly, the peptide was treated with an excess of acryloyl chloride using diisopropylethylamine, DIPEA as the base to produce the peptide crosslinker. This is shown schematically in Scheme 1 which depicts the synthesis of a peptide crosslinker containing a sequence degradable by human neutrophil elastase (HNE).

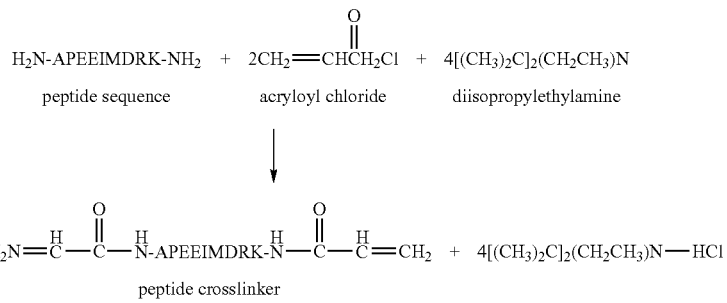

(b) Preparation of Peptide Hydrogel Film

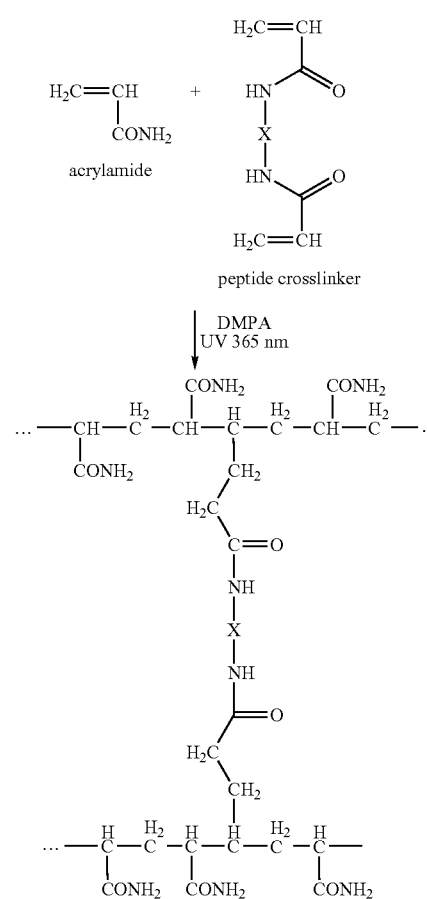

Films of peptide hydrogel were produced in situ by spin-coating a solution containing the acrylated peptide (50 mM), AAm (1.0M) and DMPA (20% by mole of AAm) in DMF, at a speed of 4500 rpm for 25 s onto the treated QCM crystals. The wet film was then illuminated with UV light (365 nm, 10 mW/cm$^2$) for 4 minutes under oxygen-free environment. The approach used is shown schematically in Scheme 2 which depicts the preparation of a peptide hydrogel.

EXAMPLE 3

Experimental Setup for QCM Impedance and EIS Measurements

High-frequency (~10 MHz) QCM admittance measurements were carried out using a Hewlett-Packard HP 8751A (5 Hz-500 MHz) Network Analyzer in reflectance mode. The electrodes were connected via a 50Ω coaxial cable and a HP 87512A transmission/reflection unit. The Network Analyzer was connected to a PC through a GPIB board (National Instruments), and the impedance data acquisition was computer controlled by a program developed in-house using LabView 6.0 (National Instruments).

For QCM measurements, one full admittance spectrum (201 points, ac stimulus 160 mV, acquisition time 1 s) was recorded over a range of 10 kHz centred at the QCM resonant frequency (~10 MHz) every 10 s.

EXAMPLE 4

Degradation Experiments

QCM crystals, one side coated with the peptide hydrogel comprising peptide sequence AAPVAAK (SEQ ID NO:2), were integrated into a custom-designed cell with the polymer-coated side in contact with the solution while the other side was kept dry. Sealing was ensured by a silicone rubber O-ring and a spring pressing from the back of the crystal. Damping of the QCM signal was reduced to a minimum by making the O-ring slightly bigger than the gold electrode. The cell was filled with 1.8 mL of phosphate buffer at pH 7.4, and the system was allowed to equilibrate for at least 30 min under magnetic stirring (700 rpm). Then, enzyme solutions (120 units mL$^{-1}$) were added using a micropipette. Degradation of the polymer films was monitored by recording the QCM admittance spectrum at regular time intervals (every 10 s). Enzyme solutions were freshly prepared, using the same phosphate buffer before each experiment in order to avoid loss of enzymatic activity. Experiments were conducted at 37° C.

The QCM admittance spectra were fitted with the BVD equivalent circuit (Sabot, A.& Krause, S. *Anal. Chem.*, 74, 3304-3311 (2002)). The variations of the electro-acoustic impedance component $\Delta X_L = \mu \Delta L$ was determined with respect to the system before degradation (with f=10 MHz). Changes in $\Delta X_L$ are directly related to the mass of the polymer film.

Results

Figure 1:
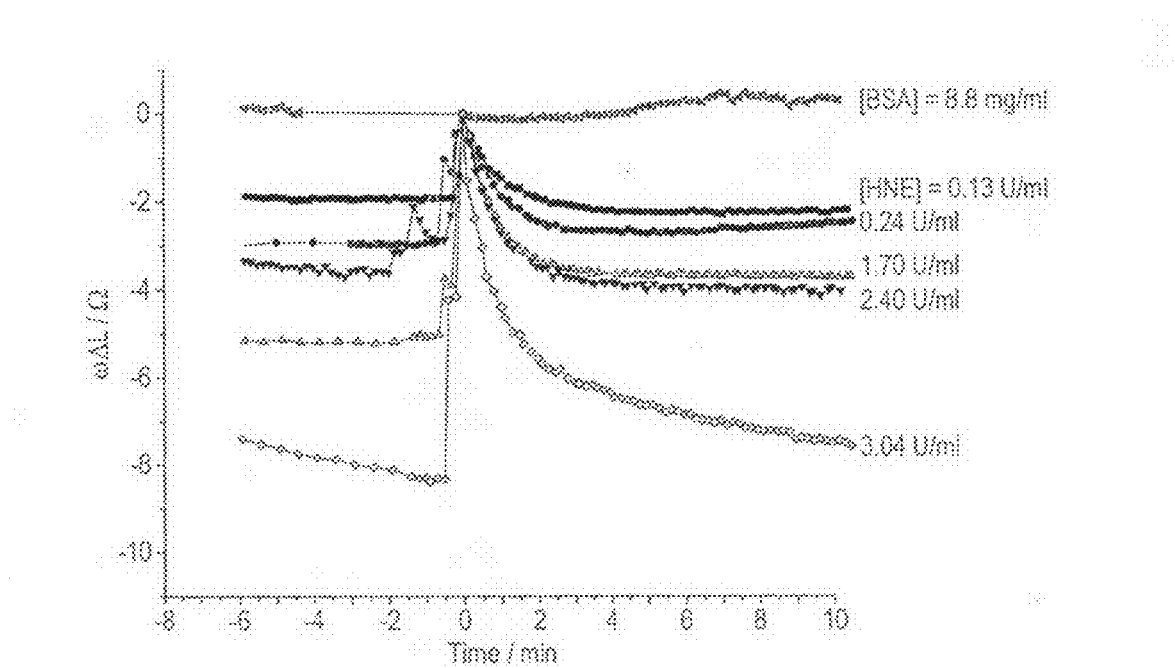
FIG. 1 shows the changes of the QCM impedance parameters $\Delta X_L = \mu \Delta L$ during the degradation of the peptide hydrogel film. The data were obtained by BVD fit of the QCM admittance spectra.
Figure 2:
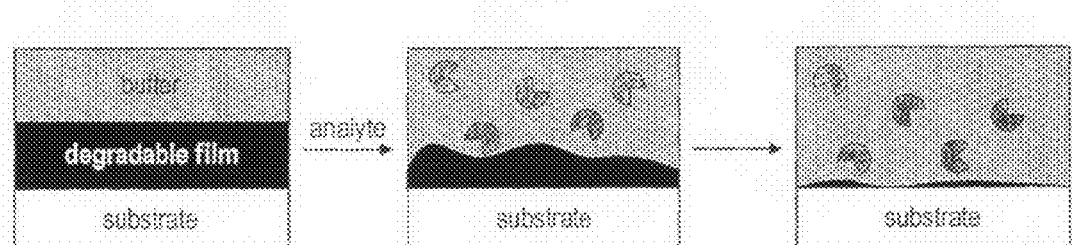
FIG. 2 shows a schematic of a biosensor based on the degradation of a thin film coating of a hydrogel polymer by a protease analyte.
Figure 3:
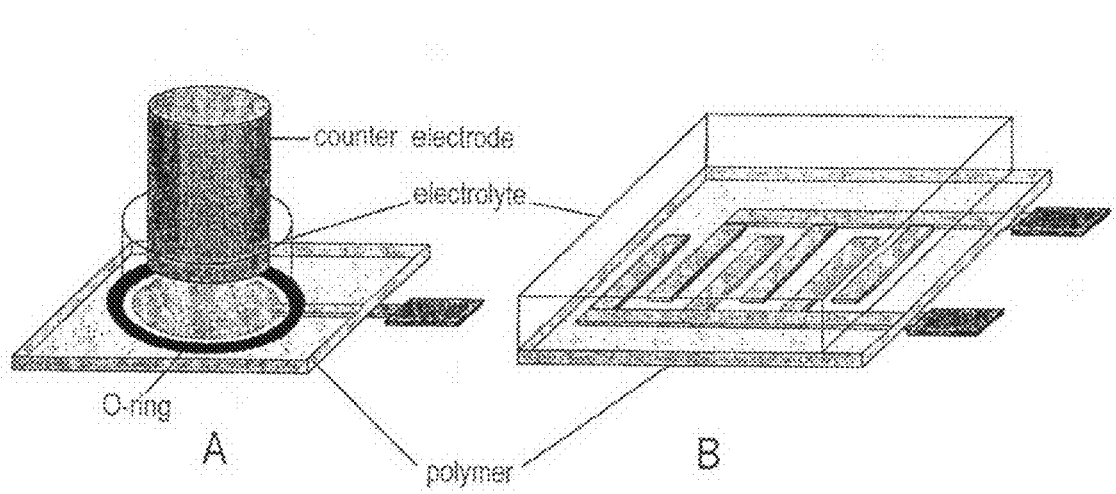
FIG. 3 shows electrode arrangements for monitoring thin film degradation by impedance measurements.
Figure 4:
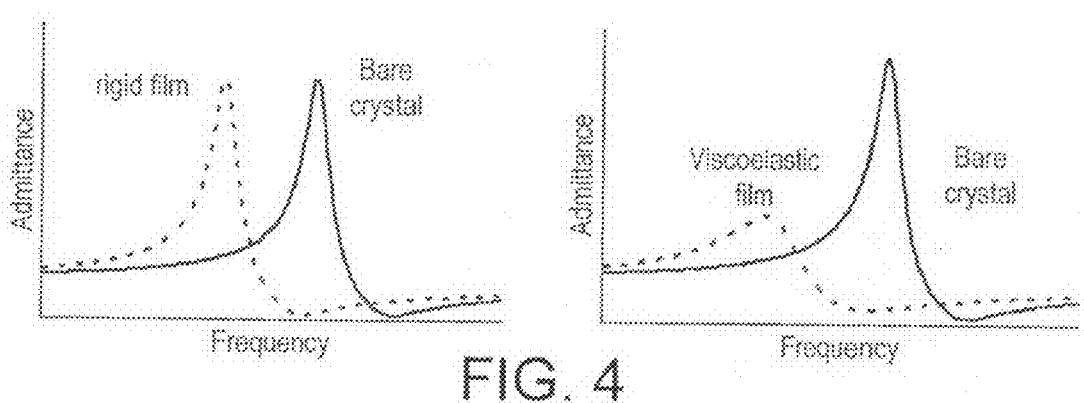
FIG. 4 shows simulated quartz crystal admittance spectra of an AT cut quartz crystal in contact with an electrolyte solution (A) shows the spectra for an uncoated crystal and a crystal coated with a rigid film. (B) shows the spectra for an uncoated crystal and a crystal coated with a viscoelastic film.

QCM admittance spectra were recorded before and after the addition of different activities of Human Neutrophil Elastase (HNE) to the buffer solution. The spectra were fitted with the BVD circuit affording the parameter $\Delta X_L$. The change of $\Delta X_L$, with time is shown in FIG. 1. The reactive inductance $\Delta X_L$ is proportional to mass changes within the film.

FIG. 1 shows that the mass of the hydrogel was constant in buffer. Upon addition of HNE, a rapid increase followed by a slower decrease in mass was observed. The sudden increase in $\Delta X_L$ can be explained with the presence of the preservative glycerol in the HNE solution. Addition of glycerol with the HNE caused an increase in the viscosity of the solution resulting in an apparent increase in mass. The gradual decrease in mass was due to the breakage of peptide bonds and the subsequent dissolution of the film resulting in mass loss from the surface of the crystal. The rate of mass loss was directly related to the enzyme activity in a range of 0.13 to 3.04 units mL$^{-1}$ of HNE".

A control experiment carried out using BSA instead of HNE showed that no change in mass was observed due to the addition of BSA (see top curve in FIG. 1), i.e. the experiment was not affected by non-specific binding.

EXAMPLE 5

Peptide hydrogels were coated onto quartz crystals as described in Example 2. The films were then conditioned at 30° C. for 8 hours. The conditioning led to higher film stability and reproducibility of the degradation in the presence of human neutrophil elastase. Degradation experiments were carried out as described in example 4. Quartz crystal admittance spectra were fitted with the BVD equivalent circuit (Sabot, A & Krause, S, Anal. Chem., 74 (2002) 3304-3311). In this example, changes in the resistive component of the BVD circuit ($\Delta R$) were monitored before and during the degradation of the hydrogel films. The resistance changes were directly related to the viscoelastic properties of the film and showed a greater sensitivity than the inductive component $\Delta X_L$. In addition to $\Delta R$, changes in the resonant frequency of the quartz crystal ($\Delta f$) were monitored before and during degradation of the hydrogel films by HNE.

Results

QCM admittance spectra were recorded before and after the addition of different activities of Human Neutrophil Elastase (HNE) to the buffer solution. The spectra were fitted with the BVD circuit affording the parameter $\Delta R$. The change of $\Delta R$ with time is shown in FIG. 14. The resistance R is a measure of the viscoelasticity of the film and is also directly related to the film thickness. A sudden increase followed by a gradual decrease in $\Delta R$ was observed. The initial increase was again due to the presence of the preservative glycerol in the HNE solution. The gradual decrease was caused by the cleavage of peptide bonds and subsequent dissolution of the hydrogel by the action of the enzyme human neutrophil elastase. The rate of degradation was determined by fitting straight lines to the curves shown in FIG. 14 in a time range from 2 min to 8 min. The resulting calibration curve is shown in FIG. 15. The rate of degradation increased with increasing elastase activity in a range of 0.72 to 30 units mL$^{-1}$ of HNE.

A similar calibration curve was obtained by monitoring changes in the resonance frequency ($\Delta f$) of the hydrogel coated quartz crystal before and during degradation. The rate of change of $\Delta f$ versus HNE activity is shown in FIG. 16. The rate of change of the resonant frequency of the hydrogel coated quartz crystal was directly related to the HNE concentration in a range of 0.72 to 30 units mL$^{-1}$ of HNE.

EXAMPLE 6

Use of Peptide Cross-Linked Dextran Hydrogels

Dextran was oxidized using a method by Ruys et al (Ruys et al, *Acta Pharmaceutica Technologica* 29, 105 (1983)). The oxidation of alcohol groups produces aldehyde groups that can be readily reacted with primary amines on the peptide of interest to form cross-links, as shown below. The carboxy terminus of each peptide sequence was modified with a lysine group to enable the peptide to cross-link via its amine terminal groups.

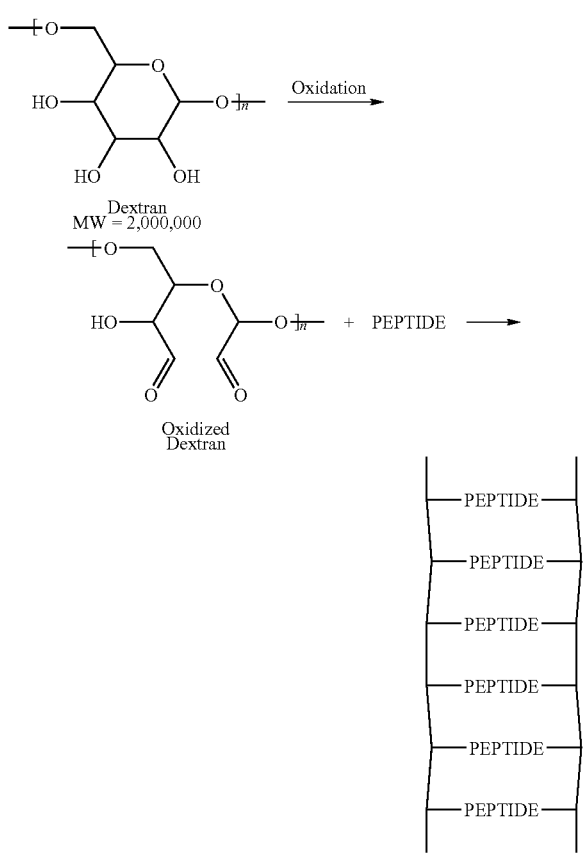

Combination 1: AAPVAAK and HNE

The first enzyme studied was HNE and the peptide sequence chosen was AAPVAAK (SEQ ID NO:2). Initial studies looked at cross-linking the dextran film and reducing the cross-linked imide bonds using $NaBH_3CN$. Hydrogel films were prepared by adding 100 μl of dextran solution (10 mg oxidized dextran/(950 μl 10 mM phosphate buffer (PB) pH 7.4+50 μl 1% Tween in water)) to a vial containing the peptide (3.08 μmoles) and reducing agent $NaBH_3CN$ (30.08 μmoles) to give 50% cross-linking of total aldehyde sites. The reaction solution was vortex mixed for 15 s and immediately added dropwise (27μl) onto a quartz crystal and spin coated at 2500 rpm for 40s. The hydrogel films were then heated at 60° C. for 1 h. The films were then conditioned in PBS (pH 7.4) for 1h and dried under $N_2$ followed by air drying overnight.

The hydrogel films were exposed to various concentrations of HNE and the degradation of the hydrogels was monitored using QCM. The films were stable in buffer for at least 30 min. FIG. 17 shows that the rate of degradation increased when the HNE concentration was increased. Hydrogel films produced this way showed relatively slow degradation in the presence of HNE.

e deposition procedure was then simplified by removing the reducing agent from the reaction solution and using 10 mM phosphate buffered saline (140 mM NaCl) (PBS) at pH 8.0 instead of PB at pH 7.4. The films were no longer heated and conditioned, but needed only to be air dried for 2 days to yield reproducible films. Stable and reproducible films were produced in this manner with using as low as 25% AAPVAAK (SEQ ID NO:2) cross-linked dextran.

The new films were also stable in buffer for at least 30 min, yet degraded more rapidly giving increased sensitivity (FIG. 18) compared to the initial deposition method. After 10 min of enzyme exposure, the film was completely degraded.

A calibration curve was constructed using various HNE concentrations (FIG. 19). There was a linear response up to 10 U/ml, yet at 20 U/ml the response started to curve, possibly indicating saturation of the degradation sites.

Combination 2: AAPFFK and Cathepsin G

Dextran hydrogel films cross-linked with AAPFFK (SEQ ID NO:7) were deposited using the second method described above for AAPVAAK (SEQ ID NO:2) and HNE. The films were similar in appearance to those cross-linked with AAPVAAK (SEQ ID NO:2).

Hydrogel films were exposed to 100 mU/ml of cathepsin G enzyme. The films took 10-20 min to stabilize in buffer. FIG. 20 shows the QCM results after exposure to cathepsin G. Cathepsin G caused the films to degrade resulting in an increase in resonant frequency. There was also a distinct increase in the maximum admittance for crystals A&B upon addition of cathepsin G (FIG. 21). FIG. 22 shows the QCM response when only buffer was added and then cathepsin G was added to the cell solution.

After degradation experiments, some film was still present on the substrate. The hydrogels were only partially degraded which may be due to availability of cleavage sites and low enzyme concentrations.

Exploring Enzyme Selectivity

The AAPFFK (SEQ ID NO:7) cross-linked dextran hydrogels were also exposed to 10 U /ml of HNE (FIG. 23). There was no noticeable degradation of the hydrogel when HNE was introduced, showing that good selectivity can be achieved by this method. Alternatively, AAPVAAK (SEQ ID NO:2) cross-linked hydrogels were exposed to 100 mU of cathepsin G (FIG. 24). In this case slow degradation was observed, indicating some minor cross-sensitivity.

The invention claimed is:

1. A method for detecting a protease, comprising:
   contacting a sample to be assayed with a detection means comprising a substrate at least partially coated with a film of a synthetic polymeric matrix; and
   measuring a signal output of said detection means;
   wherein the synthetic polymeric matrix comprises a polymer which is oxidised dextran and wherein the synthetic polymeric matrix is cross-linked with a peptide of up to 20 amino acids or wherein a peptide of up to 20 amino acids is integrated into the backbone of the synthetic polymetric matrix, wherein the synthetic polymeric matrix degrades due to the action of the protease on the peptide.

2. The method of claim 1 in which the peptide is used as a polymerisable monomer to synthesise the polymeric matrix.

3. The method of claim 1 in which the synthetic polymeric matrix is a hydrogel.

4. The method of claim 1 in which the substrate is a metal coated piezoelectric material, metallised glass, a plastic material printed with at least one carbon electrode, an electrode, a capacitor, or a transducer.

5. The method of claim 1 in which the detection means further comprises a piezoelectric quartz crystal microbalance, a metallised glass slide or an electrode.

6. The method of claim 1 in which the protease is a serine protease, a matrix metalloproteinase or a gingipain protease.

7. The method of claim 6 in which the serine protease is elastase, trypsin, chymotrypsin, subtilisin, cathepsin G, tryptase, thrombin, granzyme B, coagulation factor Xa, coagulation factor VIIa, coagulation factor IXa, coagulation factor XIa or coagulation factor XIIa.

8. The method of claim 6 in which the matrix metalloproteinase is MMP-2, MMP-8, MMP-9, or MMP-10.

9. The method of claim 6 in which the gingipain protease is arg-gingipain or lys-gingipain.

10. The method of claim 6 in which the peptide comprises the sequence:

```
                                            (SEQ ID NO: 1)
Ala-Pro-Glu-Glu-Iso-Met-Asp-Arg-Lys (APEEIMDRK), (SEQ ID NO: 2)
Ala-Ala-Pro-Val-Ala-Ala-Lys (AAPVAAK), (SEQ ID NO: 3)
Ala-Pro-Glu-Glu-Iso-Met-Asp-Arg-Glu (APEEIMDRQ), (SEQ ID NO: 4)
Ala-Pro-Glu-Glu-Iso-Met-Asp-Arg (APEEIMDR), (SEQ ID NO: 5)
Ala-Ala-Pro-Val (AAPV), (SEQ ID NO: 6)
Ala-Ala-Pro-Phe (AAPF), (SEQ ID NO: 7)
Ala-Ala-Pro-Phe-Phe-Lys (AAPFFK), (SEQ ID NO: 8)
Gly-Gly-Arg (GGR), (SEQ ID NO: 9)
Gly-Pro-Gln-Gly-Ile-Trp-Gly-Gln (GPQGIWGQ),
or (SEQ ID NO: 10)
Phe-Ala-Ala-Phe-Phe (FAAFF).
```

11. A method for detecting a protease comprising:
   contacting a sample to be assayed with a detection means comprising a substrate at least partially coated with a film of a synthetic polymeric matrix; and
   measuring a signal output of said detection means;
wherein the synthetic polymeric matrix comprises a polymer and wherein the synthetic polymeric matrix is cross-linked with a peptide of up to 20 amino acids or wherein a peptide of up to 20 amino acids is integrated into the backbone of the synthetic polymeric matrix.

12. The method of claim 5 wherein the electrode is composed of noble metals or carbon.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial
<220> FEATURE:
<223> OTHER INFORMATION: Crosslinker

<400> SEQUENCE: 1

Ala Pro Glu Glu Ile Met Asp Arg Lys
1               5
```

```
<210> SEQ ID NO 2
<211> LENGTH: 7
<212> TYPE: PRT
<213> ORGANISM: Artificial
<220> FEATURE:
<223> OTHER INFORMATION: Crosslinker

<400> SEQUENCE: 2

Ala Ala Pro Val Ala Ala Lys
1               5

<210> SEQ ID NO 3
<211> LENGTH: 9
<212> TYPE: PRT
<213> ORGANISM: Artificial
<220> FEATURE:
<223> OTHER INFORMATION: Crosslinker

<400> SEQUENCE: 3

Ala Pro Glu Glu Ile Met Asp Arg Gln
1               5

<210> SEQ ID NO 4
<211> LENGTH: 8
<212> TYPE: PRT
<213> ORGANISM: Artificial
<220> FEATURE:
<223> OTHER INFORMATION: Crosslinker

<400> SEQUENCE: 4

Ala Pro Glu Glu Ile Met Asp Arg
1               5

<210> SEQ ID NO 5
<211> LENGTH: 4
<212> TYPE: PRT
<213> ORGANISM: Artificial
<220> FEATURE:
<223> OTHER INFORMATION: Crosslinker

<400> SEQUENCE: 5

Ala Ala Pro Val
1

<210> SEQ ID NO 6
<211> LENGTH: 4
<212> TYPE: PRT
<213> ORGANISM: Artificial
<220> FEATURE:
<223> OTHER INFORMATION: Crosslinker

<400> SEQUENCE: 6

Ala Ala Pro Phe
1

<210> SEQ ID NO 7
<211> LENGTH: 6
<212> TYPE: PRT
<213> ORGANISM: Artificial
<220> FEATURE:
<223> OTHER INFORMATION: Crosslinker

<400> SEQUENCE: 7

Ala Ala Pro Phe Phe Lys
1               5
```

```
<210> SEQ ID NO 8
<211> LENGTH: 3
<212> TYPE: PRT
<213> ORGANISM: Artificial
<220> FEATURE:
<223> OTHER INFORMATION: Crosslinker

<400> SEQUENCE: 8

Gly Gly Arg
1

<210> SEQ ID NO 9
<211> LENGTH: 8
<212> TYPE: PRT
<213> ORGANISM: Artificial
<220> FEATURE:
<223> OTHER INFORMATION: Crosslinker

<400> SEQUENCE: 9

Gly Pro Gln Gly Ile Trp Gly Gln
1               5

<210> SEQ ID NO 10
<211> LENGTH: 5
<212> TYPE: PRT
<213> ORGANISM: Artificial
<220> FEATURE:
<223> OTHER INFORMATION: Crosslinker

<400> SEQUENCE: 10

Phe Ala Ala Phe Phe
1               5
```